US008754195B2

(12) United States Patent
Dimitrova et al.

(10) Patent No.: US 8,754,195 B2
(45) Date of Patent: Jun. 17, 2014

(54) ANTIBODY FORMULATIONS

(75) Inventors: Mariana N. Dimitrova, Frederick, MD (US); Neil Mody, Clarksburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 203 days.

(21) Appl. No.: 13/175,522

(22) Filed: Jul. 1, 2011

(65) Prior Publication Data

US 2012/0009199 A1 Jan. 12, 2012

Related U.S. Application Data

(60) Provisional application No. 61/361,209, filed on Jul. 2, 2010.

(51) Int. Cl.
*C07K 16/28* (2006.01)
*C07K 16/00* (2006.01)

(52) U.S. Cl.
USPC ............... 530/390.5; 530/387.1; 424/130.1

(58) Field of Classification Search
None
See application file for complete search history.

(56) References Cited

U.S. PATENT DOCUMENTS

| | | | |
|---|---|---|---|
| 6,267,958 | B1 | 7/2001 | Andya et al. |
| 7,754,859 | B2 | 7/2010 | Laing et al. |
| 2003/0113316 | A1 | 6/2003 | Kaisheva et al. |
| 2003/0165831 | A1 | 9/2003 | Lee et al. |
| 2005/0058649 | A1 | 3/2005 | Landes et al. |
| 2005/0059113 | A1 | 3/2005 | Bedian et al. |
| 2008/0089837 | A1 | 4/2008 | Laing et al. |
| 2008/0153818 | A1* | 6/2008 | Bingaman .......... 514/233.8 |

FOREIGN PATENT DOCUMENTS

| | | |
|---|---|---|
| CA | 2 560 046 A1 | 9/2005 |
| WO | WO 90/10013 A1 | 9/1990 |
| WO | WO 92/13867 A1 | 8/1992 |
| WO | WO 92/13870 A1 | 8/1992 |
| WO | WO 93/23068 A1 | 11/1993 |
| WO | WO 95/00659 A1 | 1/1995 |
| WO | WO 97/37029 A1 | 10/1997 |
| WO | WO 2005/087269 A1 | 9/2005 |
| WO | WO 2006/138729 A2 | 12/2006 |

OTHER PUBLICATIONS

Matheus et al., "A Critical Evaluation of $T_{m(FTIR)}$ Measurements of High-Concentration IgG$_1$ Antibody Formulations as a Formulation Development Tool," Pharmaceutical Research, vol. 23(7); pp. 1617-1627 (2006).
Blakey, D., "Development of a Portfolio of Antibody Based Therapeutics for Oncology," Presentation given at PEGS (2009) Protein Engineering Summit—5th Annual.
Blakey, D., "Development of novel human therapeutic antibodies targeting the IGF and PDGF signalling pathways for cancer therapy," Presentation given at ICRA (2009) International Congress on Recombinant Antibodies—8th.
Blakey, D., "The Development of a Portfolio of Antibody Based Therapeutics for Cancer Therapy," Presentation given at ELRIG (2009) European Laboratory Robotics Interest Group—Drug Discovery 2009.
Bosslet, K., "Development of a Portfolio of Antibody Based Therapeutics for Cancer Therapy," Presentation given at MipTec, 2009.
Bosslet, K., "The Development of Therapeutic Antibodies for Cancer Therapy," Presentation given at BIO (2009) Bionnale.
Davies, J., et. al., "Affinity improvement of single antibody VH domains: residues in all three hypervariable regions affect antigen binding," Immunotechnology 2(3):169-179 (1996).
Deevi, D. S., et. al., "Inhibition of human osteosarcoma xenograft growth by anti-Platelet derived growth factor receptor alpha antibody, IMC-3G3, alone and in combination with chemotherapy," Proceedings of the American Association for Cancer Research Annual Meeting, 47(Abstract 3729):877 (2006).
Gaithersburg, MD, Press release—MedImmune Advances Three Oncology Programs Into the Clinic, Aug. 10, 2009 (http://pressroom.medimmune.com/press-releases/2009/08/10/medimmune-advances-three-oncologyprograms-into-the-clinic/).
Grotendorst, et. al, "Differential Binding, Biological and Biochemical Actions of Recombinant PDGF AA, AB, and BB Molecules on Connective Tissue Cells," Journal of Cellular Physiology, 149:235-243 (1991).
Holt, L. J., et. al., "Domain antibodies: proteins for therapy," Trends in Biotechnology, 21(11):484-490 (2003).
Jermutus, L., et. al., "Challenges in the preclinical development of monoclonal antibodies," Presentation given at KS (2009) Keystone Symposia—Antibodies as Drugs (Joint Meeting).
Laing, N., et. al., "Characterization of a fully human PDGFRa antibody that reduces tumor growth and stromal infiltration in a xenograft model of non-small cell lung cancer," Eur J Cancer Suppl (20$^{th}$ EORTC-NCI-AACR Symp Mol Targets Cancer Ther—Oct. 21-24, Geneva 2008), vol. 6 (12): Abst 535.
Li, W. L., et. al., "Platelet Derived Growth Factor Receptor Alpha Is Essential for Establishing a Microenvironment That Supports Definitive Erythropoiesis," Journal of Biochemistry, 140(2):267-273 (2006).
Little, M., et. al., "Of mice and men: hybridoma and recombinant antibodies," Immunology Today, 21(8):364-370 (2000).
Loizos, N, et. al., "Targeting the platelet-derived growth factor receptor alpha with a neutralizing human monoclonal antibody inhibits the growth of tumor xenografts: implications as a potential therapeutic target," Molecular Cancer Therapeutics, 4(3):369-379 (2005).
MacDonald, T. J., et. al., "Expression profiling of medulloblastoma: PDGFRA and the RAS/MAPK pathway as therapeutic targets for metastatic disease," Nature Genetics, 29(2):143-152 (2001).
Matsui, et. al., "Isolation of a Novel Receptor cDNA Establishes the Existence of Two PDGF Receptor Genes," Science, 243:800-804 (1989).

(Continued)

*Primary Examiner* — Michael Pak

(57) ABSTRACT

The present invention relates to formulations comprising sucrose, and methods of making such formulations, wherein the sucrose content promotes the reduction or elimination of the reversible self-association (RSA) tendency of the antibody in the formulation. The present invention also relates to formulations comprising an anti-PDGFR-alpha antibody or antibody fragment. Such antibodies can be used in various methods of treatment. The application further relates to a method of eliminating or reducing the RSA tendency of antibodies in a formulation.

14 Claims, 7 Drawing Sheets

(56) References Cited

OTHER PUBLICATIONS

Figure 2A:
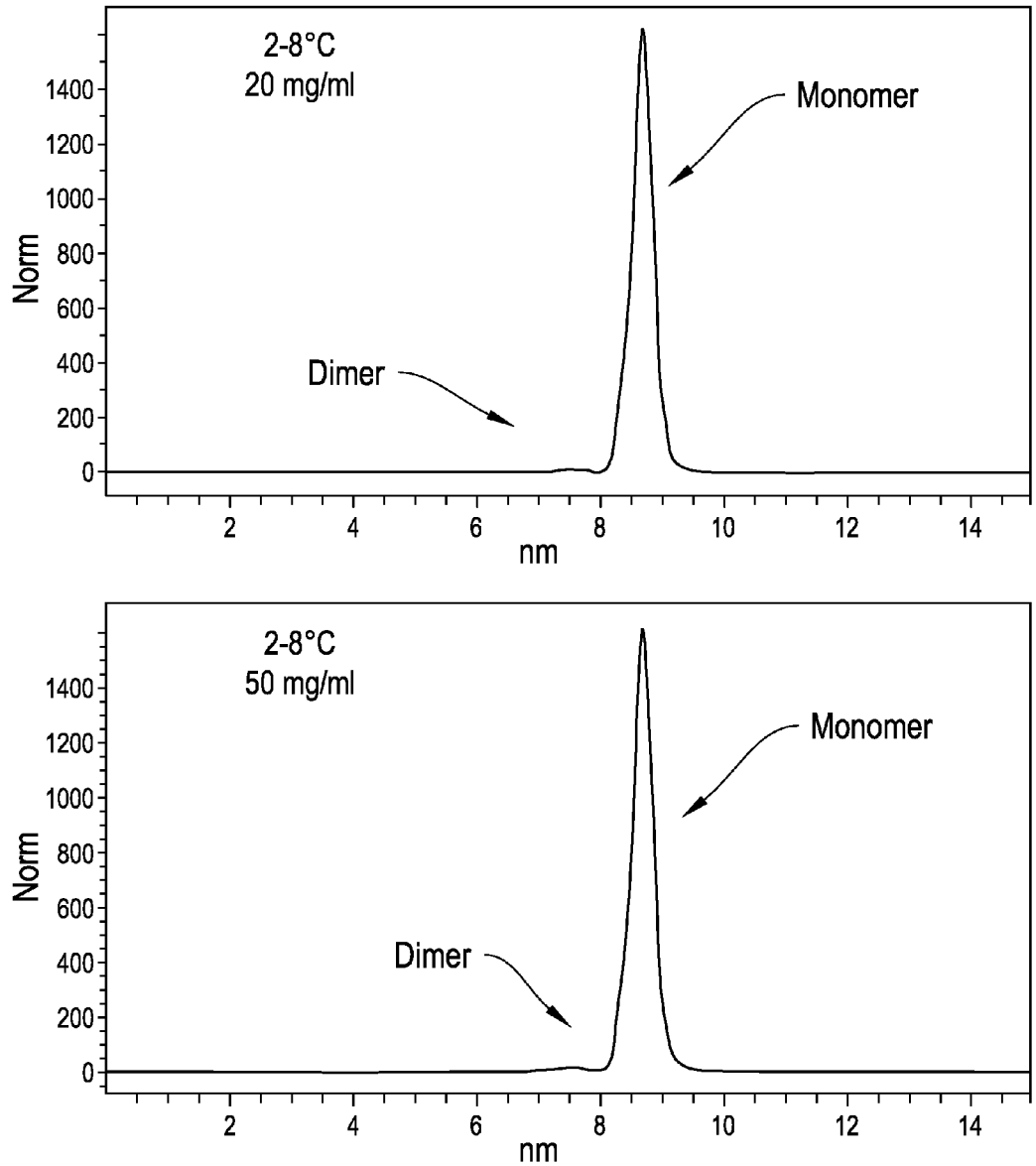

MEDI-575 clinical study ClinicalTrials.gov, "A Phase I, Multicenter, Open-label, Single-arm, Dose-escalation Study to Evaluate the Safety, Tolerability, and Antitumor Activity of MEDI-575, a Fully Human Monocional Antibody Directed Against Platelet-derived Growth Factor Receptor Alpha (PDGFRa), in Subjects With Advanced Solid Tumors Refractory to Standard Therapy or for Which No Standard Therapy Exists," Sep. 2009, Identifier: NCT00816400 (<http://clinicaltrials.gov/ct2/shown/NCT00816400>).

Müller, P., et. al., "A novel therapeutic target in human hepatocellular cancer," FASEB, Journal Fed. of American Soc. for Experimental Biology, 19(5)Suppl.S,Part2:A1505-A1506 (2005).

Steiner, P., et. al., "Inhibition of the Platelet-Derived Growth Factor Receptor Alpha (PDGFRa) Signaling Pathway with the Human Monoclonal Antibody MEDI-575 in Preclinical Mouse Models of NSCLC," Abstract from WCLC (2009) World Conference of Lung Cancer—13th.

Stock, P., et. al., "Platelet-derived growth factor receptor-alpha: a novel therapeutic target in human hepatocellular cancer," Molecular Cancer Therapeutics, 6(7):1932-1941 (2007).

Zusmanovich, M., et. al., "A Pharmacokinetic Study of Medi-575, a fully human IgG2 kappa monoclonal antibody in Cynomolgus Monkeys Following Intravenous Administration," An abstract from AAPS (2009) American Association of Pharmaceutical Scientists—2009 Annual Meeting and Exposition.

\* cited by examiner

Figure 1. MabA exhibits RSA tendency in non-sucrose-containing acetate/salt formulation
A. High Performance Size Exclusion Chromatography (HPSEC)
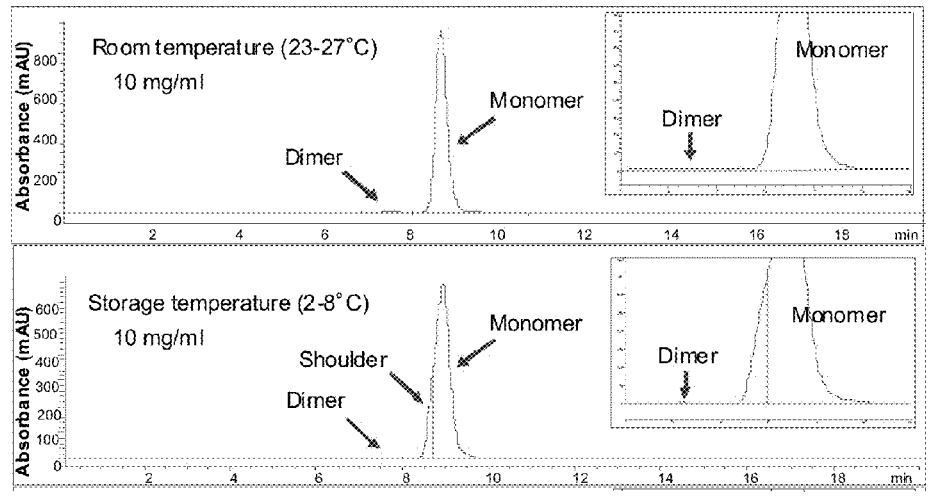
B. Analytical Ultracentrifugation (AUC)
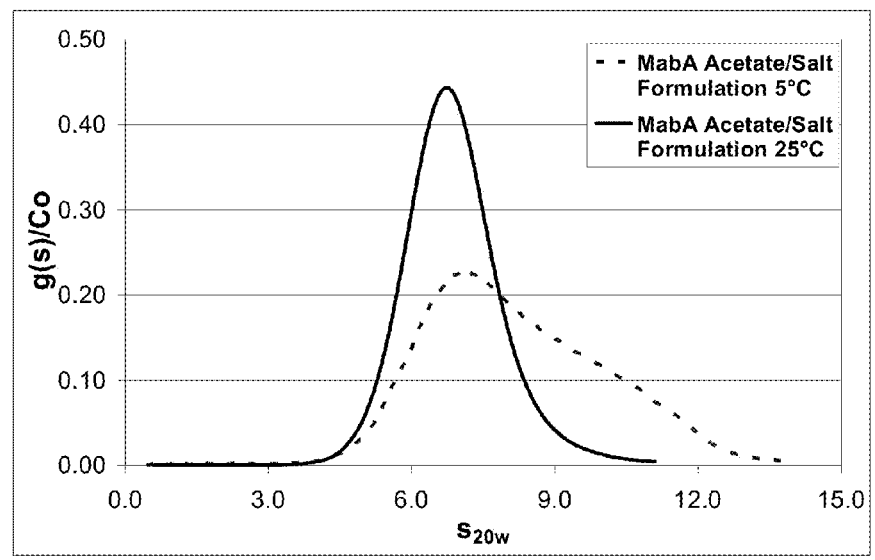

Figure 3. Interaction between ANS and hydrophobic surfaces on MabA diminish with increasing sucrose content
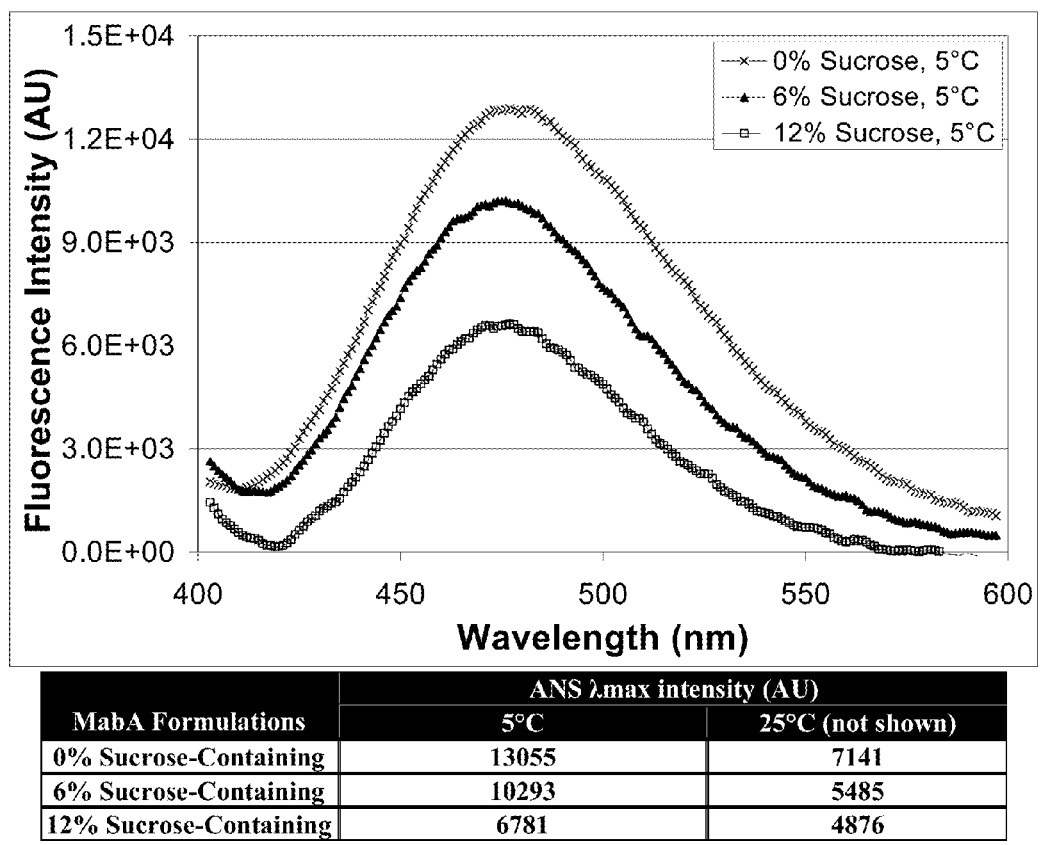
| MabA Formulations | ANS λmax intensity (AU) | |
|---|---|---|
| | 5°C | 25°C (not shown) |
| 0% Sucrose-Containing | 13055 | 7141 |
| 6% Sucrose-Containing | 10293 | 5485 |
| 12% Sucrose-Containing | 6781 | 4876 |

Figure 4. Measurement of MabA hydrodynamic radius at various temperatures in sucrose-containing or non-sucrose-containing formulations A. Non-sucrose-containing formulation B. Sucrose-containing formulation Figure 5. Enhanced thermal stability of MabA in sucrose-containing formulation
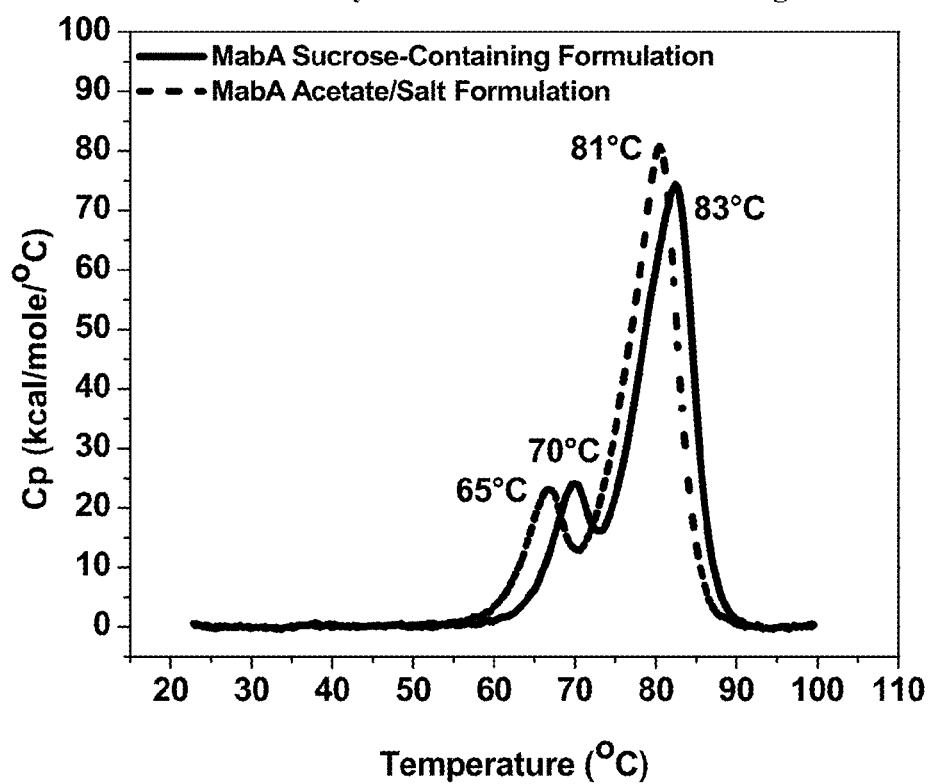

Figure 6. Sucrose-containing formulation promotes net-repulsive second virial coefficient
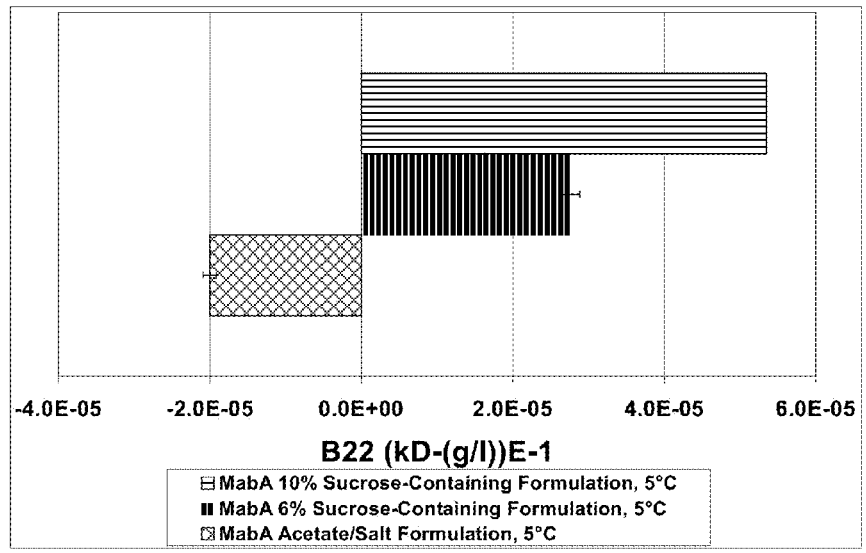
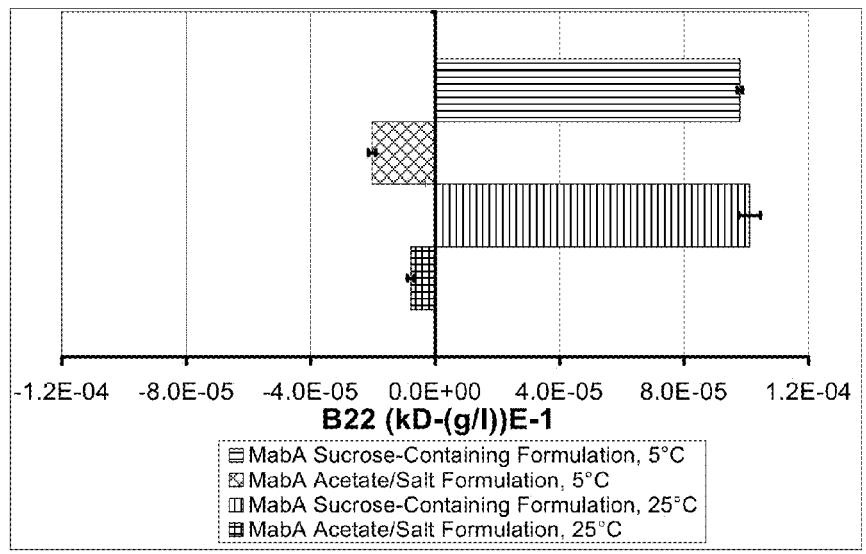

SEQUENCE LISTING

```
<160> NUMBER OF SEQ ID NOS: 8

<210> SEQ ID NO 1
<211> LENGTH: 120
<212> TYPE: PRT
<213> ORGANISM: Homo sapiens

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45
```

```
Ser Tyr Ile Ser Ser Gly Ser Ile Ile Tyr Tyr Ala Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Glu Gly Arg Ile Ala Ala Arg Gly Met Asp Val Trp Gly Gln
            100                 105                 110
Gly Thr Thr Val Thr Val Ser Ser
        115                 120

<210> SEQ ID NO 2
<211> LENGTH: 108
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
  1               5                  10                  15
Asp Arg Val Thr Ile Thr Cys Arg Pro Ser Gln Ser Phe Ser Arg Tyr
             20                  25                  30
Ile Asn Trp Tyr Gln Gln Lys Pro Gly Lys Ala Pro Lys Leu Leu Ile
         35                  40                  45
Tyr Ala Ala Ser Ser Leu Val Gly Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Thr Tyr Ser Asn Pro Pro
                 85                  90                  95
Ile Thr Phe Gly Gln Gly Thr Arg Leu Glu Ile Lys
            100                 105

<210> SEQ ID NO 3
<211> LENGTH: 10
<212> TYPE: PRT
<213> ORGANISM: Homo sapiens

<400> SEQUENCE: 3

Gly Phe Thr Phe Ser Asp Tyr Tyr Met Asn
  1               5                  10

<210> SEQ ID NO 4
<211> LENGTH: 17
<212> TYPE: PRT
<213> ORGANISM: Homo sapiens

<400> SEQUENCE: 4

Tyr Ile Ser Ser Ser Gly Ser Ile Ile Tyr Tyr Ala Asp Ser Val Lys
  1               5                  10                  15
Gly

<210> SEQ ID NO 5
<211> LENGTH: 11
<212> TYPE: PRT
<213> ORGANISM: Homo sapiens

<400> SEQUENCE: 5

Glu Gly Arg Ile Ala Ala Arg Gly Met Asp Val
  1               5                  10
```

```
<210> SEQ ID NO 6
<211> LENGTH: 11
<212> TYPE: PRT
<213> ORGANISM: Homo sapiens

<400> SEQUENCE: 6

Arg Pro Ser Gln Ser Phe Ser Arg Tyr Ile Asn
1               5                   10

<210> SEQ ID NO 7
<211> LENGTH: 7
<212> TYPE: PRT
<213> ORGANISM: Homo sapiens

<400> SEQUENCE: 7

Ala Ala Ser Ser Leu Val Gly
1               5

<210> SEQ ID NO 8
<211> LENGTH: 10
<212> TYPE: PRT
<213> ORGANISM: Homo sapiens

<400> SEQUENCE: 8

Gln Gln Thr Tyr Ser Asn Pro Pro Ile Thr
1               5                   10
```

ANTIBODY FORMULATIONS

RELATED APPLICATIONS

This application claims the benefit of U.S. provisional application 61/361,209, filed Jul. 2, 2010. The disclosure of the foregoing application is hereby incorporated by reference in its entirety.

SEQUENCE LISTING

The instant application contains a Sequence Listing which has been concurrently submitted in ASCII format via EFS-Web and is hereby incorporated by reference in its entirety. Said ASCII copy, created on Jun. 24, 2011, is named 12728101.txt and is 3,275 bytes in size.

BACKGROUND OF THE INVENTION

Instability and/or presence of undesirable species in an antibody formulation may pose problems including simple inconvenience, such as the need to store or handle the formulation in a particular way, and safety and efficacy concerns, such as those caused by increased toxicity or immunogenicity. One characteristic that is observed with some antibodies is the tendency for the antibody molecules to self-associate reversibly, also known as reversible self-association (RSA). RSA of antibodies in a given formulation may be influenced by antibody concentration, temperature and/or pH. The RSA tendency of an antibody in a formulation can have a significant impact on the physical properties of the antibody formulation, potentially affecting long-term stability, manufacturability, user compliance, and potential product safety and efficacy. For example, the RSA tendency of antibodies in some antibody formulations is significant when maintained at or below storage temperatures of about 2° C.-8° C. Although this RSA tendency may completely or substantially be resolved following extended incubation at room temperature (e.g., greater than one hour), the need for such extended incubation may negatively impact the efficient and consistent use of the formulation.

There is a need for methods to facilitate the identification of suitable formulation conditions to maximize stability and minimize RSA tendency. For example, there is a need for methods and formulations that will allow therapeutic antibodies to be stable with minimal RSA while stored at a wide range of conditions (e.g., temperature, antibody concentration and pH).

SUMMARY OF THE INVENTION

The present disclosure provides formulation methodology for reducing reversible self-association of an antibody or antibody fragment in a formulation. As such, the present disclosure provides methods that can be used to identify improved formulations for preparing antibodies and antibody fragments. Such formulations can be used, for example, therapeutically or diagnostically in a clinical or laboratory setting.

The present disclosure also provides particular formulations comprising an antibody or antibody fragment that specifically binds to PDGFR-alpha and inhibits growth of cells that express PDGFR-alpha. Exemplary formulations have advantageous RSA and stability characteristics that make the formulations particularly well suited for pharmaceutical use. In certain embodiments, the formulations are liquid formulations comprising an antibody or antibody fragment that specifically binds to PDGFR-alpha and inhibits growth of cells that express PDGFR-alpha. In one embodiment, the liquid formulation is not suitable for lyophilization. In another embodiment, the formulation is suitable for lyophilization. In certain embodiments, the formulation comprises a buffer. In other embodiments, the formulation comprises an acetate-salt buffer. In other embodiments, the formulation comprises sodium-acetate buffer. In other embodiments, the formulation comprises an acetate-salt buffer instead of or in addition to a sodium-acetate buffer. These variations to the buffers used in the formulations are applicable, in certain embodiments, to any of the aspects and embodiments of the disclosure described herein.

In another aspect, the disclosure provides a formulation, comprising: a) an aqueous carrier; b) 1 mg/ml to 100 mg/ml of an antibody or antibody fragment that specifically binds to PDGFR-alpha and inhibits growth of cells that express PDGFR-alpha; c) 4% to 20% (weight/volume) sucrose; d) 0.01% to 0.1% (weight/volume) polysorbate 80 (PS80); and e) sodium-acetate buffer, wherein said formulation has a pH of pH 4.0 to pH 6.0.

In some aspects, the disclosure provides a formulation, consisting of: a) an aqueous carrier; b) 1 mg/ml to 100 mg/ml of an antibody or antibody fragment that specifically binds to PDGFR-alpha and inhibits growth of cells that express PDGFR-alpha; c) 4% to 20% (weight/volume) sucrose; d) 0.01% to 0.1% (weight/volume) polysorbate 80 (PS80); and e) sodium-acetate buffer, wherein said formulation has a pH of pH 4.0 to pH 6.0.

In certain embodiments of any of the foregoing, the antibody or antibody fragment comprises a full length IgG monoclonal antibody. In some embodiments, said antibody or antibody fragment is present at a concentration of from 20 mg/ml to 50 mg/ml. In certain embodiments, the antibody or antibody fragment is present at a concentration of 20 mg/ml. In other embodiments, the antibody or antibody fragment is present at a concentration of 50 mg/ml.

In certain embodiments of any of the foregoing aspects and embodiments, the antibody or antibody fragment comprises a heavy chain polypeptide comprising the amino acid sequence of SEQ ID NO: 1. In some embodiments, the antibody or antibody fragment comprises a light chain polypeptide comprising the amino acid sequence of SEQ ID NO: 2. In certain embodiments, the antibody or antibody fragment binds to the same epitope as an antibody comprising a heavy chain polypeptide comprising the amino acid sequence of SEQ ID NO: 1 and a light chain polypeptide comprising the amino acid sequence of SEQ ID NO: 2.

In certain embodiments of any of the foregoing aspects and embodiments, the antibody or antibody fragment comprises: a VH CDR1 having the amino acid sequence of SEQ ID NO: 3; a VH CDR2 having the amino acid sequence of SEQ ID NO: 4; a VH CDR3 having the amino acid sequence of SEQ ID NO: 5;a VL CDR1 having the amino acid sequence of SEQ ID NO: 6; a VL CDR2 having the amino acid sequence of SEQ ID NO: 7; and a VL CDR3 having the amino acid sequence of SEQ ID NO: 8.

In certain embodiments of any of the foregoing aspects and embodiments, the antibody or antibody fragment binds to the same epitope as an antibody comprising: a VH CDR1 having the amino acid sequence of SEQ ID NO: 3; a VH CDR2 having the amino acid sequence of SEQ ID NO: 4; a VH CDR3 having the amino acid sequence of SEQ ID NO: 5;a VL CDR1 having the amino acid sequence of SEQ ID NO: 6; a VL CDR2 having the amino acid sequence of SEQ ID NO: 7; and a VL CDR3 having the amino acid sequence of SEQ ID NO: 8.

In certain embodiments of any of the foregoing aspects and embodiments, the formulation comprises 6% (w/v) sucrose or 10% (w/v) sucrose. In certain embodiments, the formulation comprises 0.05% (w/v) PS80. In some embodiments, the formulation comprises 50 mM sodium-acetate buffer. In other embodiments, the formulation has a pH of 5.5.

In certain embodiments of any of the foregoing aspects and embodiments, said antibody or antibody fragment in said formulation has substantially similar reversible self-association (RSA) characteristics at 2-8° C. and 23-27° C., as determined by analytical ultracentrifugation (AUC). In certain embodiments, RSA of said antibody or antibody fragment in said formulation is undetectable by high-performance size exclusion chromatography (HPSEC) and dynamic light scattering (DLS).

In certain embodiments of any of the foregoing aspects and embodiments, greater than 95% of said antibody or antibody fragment in said formulation is in a monomeric form, and RSA of said antibody or antibody fragment is undetectable by HPSEC at 2-8° C. when assessed at 10 mg/ml. In some embodiments, the hydrodynamic radius of said antibody or antibody fragment in said formulation does not differ significantly at 5° C. versus 25° C., as determined by dynamic light scattering (DLS).

In certain embodiments of any of the foregoing aspects and embodiments, the formulation is suitable for intravenous administration. In certain embodiments, the aqueous carrier is water. In some embodiments, the formulation is non-pyrogenic. In other embodiments, the formulation further comprises a preservative to extend shelf-life. In some embodiments, the formulation is stable at 2-8° C. for at least 2 years as determined by high performance size exclusion chromatography (HPSEC). In some embodiments, purity of said formulation decreases by less than 0.5% per year for at least two years as determined by high performance size exclusion chromatography (HPSEC).

In certain embodiments of any of the foregoing aspects and embodiments, the formulation is substantially free of histidine, any additional surfactant, any additional saccharide or polyol, and/or any additional salt.

In certain embodiments of any of the foregoing aspects and embodiments, the formulation is suitable for lyophilization. In other embodiments, the formulation is not suitable for lyophilization.

In some aspects, the present disclosure provides a formulation, consisting essentially of: a) sterile water; b) 20 mg/ml of an antibody or antibody fragment that specifically binds to PDGFR-alpha and inhibits growth of cells that express PDGFR-alpha; c) 10% (weight/volume) sucrose; d) 0.05% (weight/volume) polysorbate 80 (PS80); and e) 50 mM sodium-acetate buffer, wherein said formulation has a pH of pH 5.5.

In another aspect, the present disclosure provides a formulation, consisting essentially of: a) sterile water; b) 50 mg/ml of an antibody or antibody fragment that specifically binds to PDGFR-alpha and inhibits growth of cells that express PDGFR-alpha; c) 10% (weight/volume) sucrose; d) 0.05% (weight/volume) polysorbate 80 (PS80); and e) 50 mM sodium-acetate buffer, wherein said formulation has a pH of pH 5.5.

In certain embodiments of any of the foregoing aspects and embodiments, the antibody or antibody fragment comprises a heavy chain polypeptide comprising the amino acid sequence of SEQ ID NO: 1. In some embodiments, the antibody or antibody fragment comprises a light chain polypeptide comprising the amino acid sequence of SEQ ID NO: 2. In certain embodiments, the antibody or antibody fragment binds to the same epitope as an antibody comprising a heavy chain polypeptide comprising the amino acid sequence of SEQ ID NO: 1 and a light chain polypeptide comprising the amino acid sequence of SEQ ID NO: 2.

In certain embodiments of any of the foregoing aspects and embodiments, the antibody or antibody fragment comprises: a VH CDR1 having the amino acid sequence of SEQ ID NO: 3; a VH CDR2 having the amino acid sequence of SEQ ID NO: 4; a VH CDR3 having the amino acid sequence of SEQ ID NO: 5:a VL CDR1 having the amino acid sequence of SEQ ID NO: 6; a VL CDR2 having the amino acid sequence of SEQ ID NO: 7; and a VL CDR3 having the amino acid sequence of SEQ ID NO: 8.

In certain embodiments of any of the foregoing aspects and embodiments, the antibody or antibody fragment binds to the same epitope as an antibody comprising: a VH CDR1 having the amino acid sequence of SEQ ID NO: 3; a VH CDR2 having the amino acid sequence of SEQ ID NO: 4; a VH CDR3 having the amino acid sequence of SEQ ID NO: 5:a VL CDR1 having the amino acid sequence of SEQ ID NO: 6; a VL CDR2 having the amino acid sequence of SEQ ID NO: 7; and a VL CDR3 having the amino acid sequence of SEQ ID NO: 8.

In certain embodiments of any of the foregoing aspects and embodiments, said antibody or antibody fragment in said formulation has substantially similar non-reversible self-association (non-RSA) characteristics at 2-8° C. and 23-27° C., as determined by AUC. In some embodiments, RSA of said antibody or antibody fragment in said formulation is undetectable by HPSEC at 2-8° C. when assessed at 10 mg/ml. In other embodiments, greater than 95% of said antibody or antibody fragment in said formulation is in a monomeric form at 2-8° C. In certain embodiments, the hydrodynamic radius of said antibody or antibody fragment in said formulation does not differ significantly at 5° C. versus 25° C., as determined by dynamic light scattering (DLS).

In certain embodiments of any of the foregoing aspects and embodiments, the formulation is suitable for intravenous administration. In some embodiments, the water is sterile water. In certain embodiments, the formulation is non-pyrogenic.

In certain embodiments of any of the foregoing aspects and embodiments, the formulation is stable at about 2 to 8° C. for at least 2 years as determined by long term stability studies following ICHQ1A guidelines. The ICHQ1A guidelines are industry standards (Federal Register, Vol, 68, No. 225, Friday, Nov. 21, 2003; pages 65717-18). In certain embodiments, purity of said formulation decreases by less than 0.5% per year for at least two years as determined by high performance size exclusion chromatography (HPSEC).

In certain embodiments of any of the foregoing aspects and embodiments, the formulation is not suitable for lyophilization. In some embodiments, the formulation is suitable for lyophilization.

In another aspect, the present disclosure provides a formulation, comprising: a) an aqueous carrier; b) 1 mg/ml to 100 mg/ml of an antibody or antibody fragment; c) 4% to 20% (weight/volume) sucrose; d) 0.01% to 0.1% (weight/volume) polysorbate 80 (PS80); and e) sodium-acetate buffer, wherein said formulation has a pH of pH 4.0 to pH 6.0, and wherein said antibody or antibody fragment in said formulation has substantially the same non-RSA tendency when evaluated at about 2-8° C. versus at about 23-27° C. In other aspects, the present disclosure provides a formulation, comprising: a) an aqueous carrier; b) 1 mg/ml to 100 mg/ml of an antibody or antibody fragment; c) 4% to 20% (weight/volume) sucrose; d) 0.01% to 0.1% (weight/volume) polysorbate 80 (PS80); and e) sodium-acetate buffer, wherein said formulation has a pH of pH 4.0 to pH 6.0, and wherein greater than 95% of said antibody or antibody fragment in said formulation is in non-self-associated, monomeric form at 2-8° C.

In certain aspects, the present disclosure provides a formulation, consisting of: a) an aqueous carrier; b) 1 mg/ml to 100 mg/ml of an antibody or antibody fragment; c) 4% to 20% (weight/volume) sucrose; d) 0.01% to 0.1% (weight/volume) polysorbate 80 (PS80); and e) sodium-acetate buffer, wherein said formulation has a pH of pH 4.0 to pH 6.0, and wherein said antibody or antibody fragment in said formulation has substantially the same non-RSA tendency when evaluated at about 2-8° C. versus at about 23-27° C.

In some aspects, the present disclosure provides a formulation, consisting of: a) an aqueous carrier; b) 1 mg/ml to 100 mg/ml of an antibody or antibody fragment; c) 4% to 20% (weight/volume) sucrose; d) 0.01% to 0.1% (weight/volume) polysorbate 80 (PS80); and e) sodium-acetate buffer, wherein said formulation has a pH of pH 4.0 to pH 6.0, and wherein greater than 95% of said antibody or antibody fragment in said formulation is in non-self-associated, monomeric form at 2-8° C.

In certain embodiments of any of the foregoing, the disclosure provides formulations in which sodium-acetate buffer is replaced or substituted with a different acetate-salt buffer. For example, in certain embodiments, the disclosure provides formulations that comprise a different acetate-salt buffer instead of sodium-acetate. When a different acetate-salt buffer is used, the buffer may be used analogously to the way in which sodium-acetate buffer is used (e.g., at or across the same range of concentrations). In other embodiments, the formulation comprises more than one acetate-salt buffer.

In further aspects, the present disclosure provides a method of eliminating or reducing reversible self-association (RSA) of an antibody in a formulation, comprising: providing an initial formulation comprising an antibody or antibody fragment, wherein RSA of said antibody or antibody fragment in said initial formulation is measurable by HPSEC i) at approximately 2-8° C. and/or ii) at a concentration of greater than 4 mg/ml, and which antibody or antibody fragment in said initial formulation contains high molecular weight forms; adding sucrose to said initial formulation to provide an altered formulation having about 4% to about 20% (weight/volume) sucrose, wherein RSA of the antibody or antibody fragment in the altered formulation is eliminated or reduced relative to that of the initial formulation, when compared at a given antibody concentration at approximately 2-8° C.

In certain embodiments, the method further comprises: assaying hydrodynamic radius of said antibody or antibody fragment in said altered formulation and comparing said hydrodynamic radius to that of said antibody or antibody fragment in said initial formulation, wherein the hydrodynamic radius of said antibody or antibody fragment in said altered formulation is eliminated or reduced relative to that in said initial formulation, when compared at a given antibody concentration at approximately 2-8° C. In one embodiment, hydrodynamic radius of said altered formulation is assayed by DLS.

In certain embodiments of any of the foregoing aspects and embodiments, the method further comprises: assaying RSA tendency of said antibody or antibody fragment in said altered formulation using HPSEC, and comparing said RSA tendency to that of said antibody or antibody fragment in said initial formulation, wherein the RSA tendency of said antibody or antibody fragment in said altered formulation is eliminated or reduced relative to that in said initial formulation, when compared at a given antibody concentration at approximately 2-8° C. In certain embodiments, the method further comprises assaying RSA tendency of said antibody or antibody fragment in said altered formulation at approximately 2-8° C. and at approximately 23-27° C., and confirming that the antibody or antibody fragment in said altered formulation has substantially similar non-RSA tendency at 2-8° C. and 23-27° C. In one embodiment, assaying RSA tendency at approximately 2-8° C. and at approximately 23-27° C. is by AUC. In some embodiments, RSA of said antibody or antibody fragment in said altered formulation is undetectable by HPSEC.

In certain embodiments of any of the foregoing aspects and embodiments, the antibody or antibody fragment is present in the initial formulation and in the altered formulation at a concentration of from about 1 mg/ml to about 100 mg/ml. In some embodiments, the antibody or antibody fragment is present in the initial formulation and in the altered formulation at a concentration of about 20 mg/ml or of about 50 mg/ml. In other embodiments, the antibody or antibody fragment is present in the altered formulation at a concentration of about 20 mg/ml, or of about 50 mg/ml.

In certain embodiments of any of the foregoing aspects and embodiments, adding sucrose to the initial formulation comprises adding sucrose to achieve a final concentration of sucrose in the altered formulation of about 10% (w/v).

In other aspects, the present disclosure provides a method of eliminating or reducing reversible self-association (RSA) of an antibody in a formulation, comprising: a) providing an initial formulation comprising an antibody or antibody fragment, wherein RSA of said antibody or antibody fragment in said initial formulation is detectable by HPSEC at approximately 2-8° C. when assessed at a concentration of 10 mg/ml; b) assaying a biophysical property of said antibody or antibody fragment in said initial formulation using one or more assays; c) adjusting sucrose content of said initial formulation to achieve a final concentration from about 4% to about 20% (w/v) to produce an altered formulation; and d) assaying a biophysical property of said antibody or antibody fragment in said altered formulation using one or more assays; wherein RSA of the antibody or antibody fragment in the altered formulation is eliminated relative to that of the initial formulation, when compared at a given antibody concentration at approximately 2-8° C.

In some embodiments, step (c) is performed more than one time. In certain embodiments, steps (c) and (d) are performed more than one time. In other embodiments, steps (b) and (d) comprise evaluating the same biophysical property. In an exemplary embodiment, the biophysical property is a signature chromatographic peak indicative of RSA tendency, as determined by high-performance size exclusion chromatography (HPSEC). In some embodiments, the signature chromatographic peak is presence of a shoulder in said peak. In some embodiments, said biophysical property is evaluated at two different temperatures.

In certain embodiments of any of the foregoing aspects and embodiments, said biophysical property is the hydrodynamic radius of the antibody or antibody fragment in said initial formulation and/or said altered formulation, as determined by dynamic light scattering.

In certain embodiments of any of the foregoing aspects or embodiment, said biophysical property is hydrodynamic radius, and the method comprises assaying hydrodynamic radius of said antibody or antibody fragment in said altered formulation and comparing said hydrodynamic radius to that of said antibody or antibody fragment in said initial formulation, wherein the hydrodynamic radius of said antibody or antibody fragment in said altered formulation is reduced relative to that in said initial formulation, when compared at a given antibody concentration at approximately 2-8° C. In an exemplary embodiment, the hydrodynamic radius of said altered formulation is assayed by DLS.

In certain embodiments of any of the foregoing aspects or embodiments, the antibody or antibody fragment is present in the initial formulation and in the altered formulation at a concentration of from about 1 mg/ml to about 100 mg/ml. In certain embodiments, the antibody or antibody fragment is present in the initial formulation and in the altered formulation at a concentration of about 20 mg/ml, or about 50 mg/ml. In some embodiments, the antibody or antibody fragment is present in the altered formulation at a concentration of about 20 mg/ml, or about 50 mg/ml.

In certain embodiments of any of the foregoing aspects and embodiments, adjusting sucrose content comprises adding sucrose to achieve a final concentration of sucrose in the altered formulation of about 10% (w/v).

In other aspects, the present disclosure provides a formulation comprising an antibody or antibody fragment produced according to the methods of any of the foregoing aspects or embodiments.

In further aspects, the present disclosure provides a method of treating a neoplastic condition in a patient in need thereof, comprising administering to said patient in need thereof an effective amount of the formulation of any of the foregoing aspects or embodiments. In certain embodiments, the formulation is administered as part of a therapeutic regimen in combination with one or more additional agents or treatment modalities. In an exemplary embodiment, the neoplastic condition is cancer.

In another aspect, the present disclosure provides a method for producing a formulation comprising an antibody or antibody fragment having reduced RSA, the method comprising: producing an antibody or antibody fragment; and formulating said antibody or antibody fragment as a formulation comprising: an aqueous carrier; 1 mg/ml to 100 mg/ml of said antibody or antibody fragment; 4% to 20% (weight/volume) sucrose; 0.01% to 0.1% (weight/volume) surfactant; and acetate-salt buffer, wherein said formulation has a pH of pH 4.0 to pH 6.0; wherein the amount of sucrose for use in said formulation was selected by: providing an initial formulation comprising an antibody or antibody fragment, wherein RSA of said antibody or antibody fragment in said initial formulation was detectable by HPSEC at approximately 2-8° C., and which antibody or antibody fragment in said initial formulation consists of high molecular weight forms; adding sucrose to said initial formulation to provide an altered formulation having 4% to 20% (weight/volume) sucrose, wherein RSA of the antibody or antibody fragment in the altered formulation was reduced relative to the initial formulation, when compared at a given antibody concentration at approximately 2-8° C.

In other aspects, the present disclosure provides a method for producing a formulation comprising an antibody or antibody fragment having reduced RSA, the method comprising: producing an antibody or antibody fragment; and formulating said antibody or antibody fragment as a formulation comprising an aqueous carrier; 1 mg/ml to 100 mg/ml of said antibody or antibody fragment; 4% to 20% (weight/volume) sucrose; 0.01% to 0.1% (weight/volume) surfactant; and acetate-salt buffer, wherein said formulation has a pH of pH 4.0 to pH 6.0; wherein the amount of sucrose for use in said formulation was selected by: a) providing an initial formulation comprising an antibody or antibody fragment, wherein RSA of said antibody or antibody fragment in said initial formulation was detectable by HPSEC at approximately 2-8° C. when assessed at 10 mg/ml; b) assaying a biophysical property of said antibody or antibody fragment in said initial formulation using one or more assays; c) adjusting sucrose content of said initial formulation to achieve a final concentration from about 4% to about 40% (w/v) to produce an altered formulation; and d) assaying a biophysical property of said antibody or antibody fragment in said altered formulation using one or more assays, wherein RSA of the antibody or antibody fragment in the altered formulation was reduced relative to that of the initial formulation, when compared at a given antibody concentration at approximately 2-8° C.

In certain embodiments of any of the foregoing, the disclosure provides formulations and methods in which there is a buffer in the formulation. In certain embodiments, the buffer is an acetate-salt buffer. In certain embodiments, the acetate-salt buffer is a sodium-acetate buffer. In other embodiments, the acetate-salt buffer is not a sodium-acetate buffer. In other embodiments, sodium-acetate buffer is replaced or substituted with a different acetate-salt buffer. For example, in certain embodiments, the disclosure provides formulations that comprise a different acetate-salt buffer instead of sodium-acetate. When a different acetate-salt buffer is used, the buffer may be used analogously to the way in which sodium-acetate buffer is used (e.g., at or across the same range of concentrations). In other embodiments, the formulation comprises more than one acetate-salt buffer.

The disclosure contemplates all combinations of any of the foregoing aspects and embodiments, as well as combinations with any of the embodiments set forth in the detailed description and examples. Moreover, when reference is made to "any of the foregoing aspects or embodiments", it should also be understood to include "any of the foregoing or following aspects or embodiments."

BRIEF DESCRIPTION OF THE TABLES AND FIGURES

FIG. 1. MabA exhibits RSA tendency in the non-sucrose containing acetate/salt formulation. RSA tendency of this antibody in this initial, acetate/salt containing formulation was determined by HPSEC and sedimentation velocity analytical ultracentrifugation (AUC). FIG. 1A, lower panel (2-8° C.), indicates the presence of a shoulder at the leading edge of the peak indicative of RSA under storage temperature conditions. The vertical line in the monomer peak at 2-8° C. is shown to illustrate the self-association. FIG. 1B shows that while MabA in this non-sucrose containing formulation sediments over a discrete range at 23-27° C., significant broadening and higher sedimentation coefficient is seen at 2-8° C., indicative of RSA. FIG. 1 shows that MabA, in an initial non-sucrose containing formulation, has RSA tendency at 2-8° C. that is measurable by HPSEC and AUC. The RSA occurs predominately as dimerization and higher order oligomerization. Moreover, FIG. 1 shows that RSA tendency of this antibody in this initial formulation is temperature dependent (e.g., RSA tendency, as evidenced by the above referenced shoulder, dissociates to a monomer at room temperature relative to storage temperatures of about 2-8° C.).

Figure 2B:
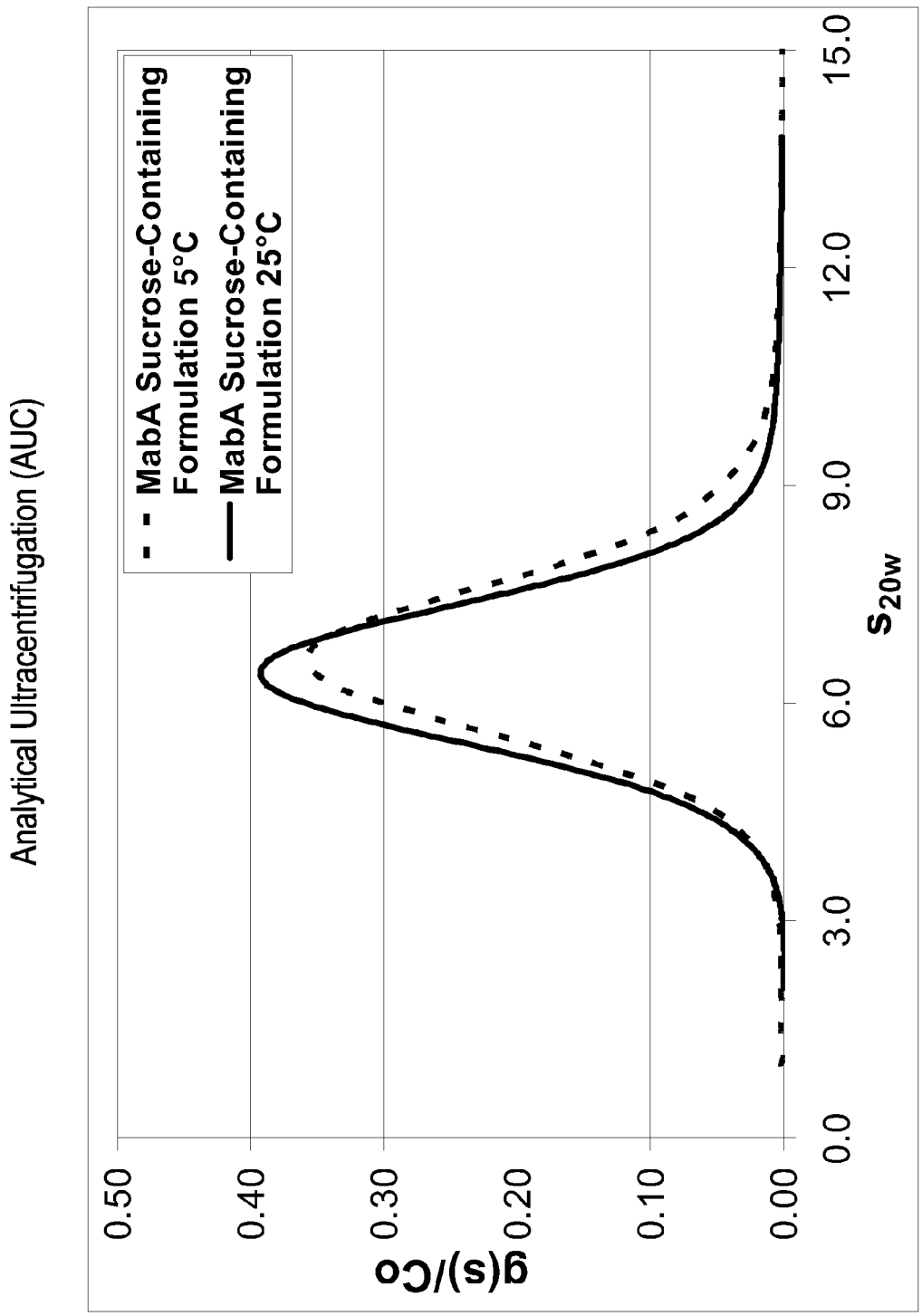

FIG. 2. Prevention of RSA of MabA in the sucrose-containing formulation as determined by HPSEC and AUC. In the sucrose-containing formulation, RSA was not detected, as determined by HPSEC (FIG. 2A) at 2-8° C., at both 20 mg/ml and 50 mg/ml antibody concentrations. Further, as demonstrated by AUC, no temperature dependence was observed in antibody sedimentation (superimposed AUC sedimentation profiles at 2-8° C. and 23-27° C.; see FIG. 2B). Thus, in comparison to the non-sucrose containing formulation, RSA of MabA was prevented when provided in the sucrose-containing formulation. For example, RSA was no longer detected and measurable by HPSEC at about 2-8° C.

FIG. 3. Interactions between α-amino naphthalene trisulfonic acid (ANS) and hydrophobic surfaces on MabA diminish with increasing sucrose content. A comparison of 0% and 12% sucrose content shows significantly reduced ANS binding in the sucrose containing formulation, suggesting that sucrose content decreases surface hydrophobicity of the antibody, resulting in reduced RSA.

FIG. 4. Measurement of MabA hydrodynamic radius at various temperatures in sucrose-containing and non-sucrose-containing formulations. FIG. 4A illustrates the hydrodynamic radius of MabA in acetate/salt-containing formulation at 5° C., 25° C., and 37° C. In the absence of sucrose, the antibody's hydrodynamic radius is temperature dependent, indicative of RSA tendency at low temperature. However, in the presence of sucrose (FIG. 4B), no temperature dependence is observed, indicative of the elimination of RSA tendency.

FIG. 5. Enhanced thermal stability of MabA in sucrose-containing formulation. Using differential scanning calorimetry (DSC), MabA thermal stability was evaluated in sucrose-containing and non-sucrose-containing formulations. The antibody shows significantly greater thermal stability in the sucrose-containing formulation. This shows that the sucrose-containing formulation had induced favorable conformational change resulting in both reduced RSA and increased thermal stability relative to the initial formulation.

FIG. 6. Measurement of second virial coefficient. The addition of sucrose shifts the second virial coefficient from attractive to repulsive net interactions. The results suggest that sucrose contributes to significant reduction/prevention of the intermolecular interactions and the propensity for self-association.

DETAILED DESCRIPTION (i) Overview

Reversible self-association of antibodies may occur under certain formulation conditions. Typically, however, reversible self-association of antibodies in a formulation occurs as just part of a larger problem of protein aggregation. For example, reversible self-association may be observed in a context and/or under conditions in which significant non-reversible dimerization, trimerization and other higher order oligomerization occur. Presence of significant non-reversible aggregation generally makes a formulation unsuited for therapeutic use.

Additionally or alternatively, measurable reversible self-association occurs only at very low temperatures that are substantially below the temperatures at which the formulation is stored or used. In this context, although reversible self-association is measurable under conditions of very low temperature, the absence of measurable self-association at storage and room temperature means that RSA may not substantially impact the diagnostic, research or therapeutic utility of the formulation.

In either of the above situations, there may not be a particular need to modulate the formulation to reduce RSA. However, in some contexts, measurable reversible self-association of antibodies in a formulation occurs at storage temperatures (approximately 2-8° C., such as 5° C.). Alternatively or additionally, measurable reversible self-association of antibodies in a formulation still occurs—even at relatively low antibody concentration (e.g., about 4-8 mg/ml). This is significant because reversible self-association is expected to decrease with decreasing antibody concentration, and the presence of detectable RSA at doses well below typical storage or use conditions suggests that RSA may be a significant issue for that antibody in that formulation at standard therapeutic or use conditions. The present disclosure provides methods to prevent or reduce RSA and challenges associated with RSA in these contexts.

The present disclosure is based, in part, on the discovery that sucrose reduces or prevents the RSA of an anti-PDGFR-alpha antibody in a formulation as described herein. Accordingly, in certain aspects, the present disclosure provides methods for mitigating RSA tendency of an antibody or antibody fragment in a formulation. Amongst the observed benefits of the formulation approaches described herein is the ability to prepare formulations in which the RSA tendency of antibodies in the formulation is not detected by HPSEC when assessed at a given concentration, such as at least about 10 mg/ml, and is substantially the same at storage temperature and at room temperature. In certain embodiments, the methods result in preparation of a formulation in which the RSA tendency of antibodies in the formulation is not measurable by HPSEC at storage temperatures of approximately 2-8° C. It is noted that RSA tendency may be evaluated at any of a number of concentrations and temperatures. However, evaluation of RSA tendency at too low of an antibody condition may falsely underestimate the presence of RSA. Accordingly, before concluding the elimination of RSA tendency or significant improvement of RSA tendency for an antibody in a formulation, assessment by HPSEC and/or AUC should be conducted at target formulation concentrations or a concentration of at least about 10 mg/ml and at 2-8° C. RSA that is not detectable by HPSEC and/or AUC at such a concentration and temperature range is consistent with the conclusion that RSA is eliminated for the antibody in the formulation.

One of the significant benefits of the methods and compositions of the present disclosure is that formulations in which RSA is not detected by HPSEC, particularly when assessed at a relevant concentration such as at least 10 mg/ml, and which does not significantly differ between storage temperature (2-8° C.) and room temperature and/or formulations in which RSA tendency is not measurable at 2-8° C. by HPSEC when assessed at a relevant concentration such as at least 10 mg/ml can be used without the need for extended incubation at room temperature. In other words, an extended period of 60-90 minutes or more of room temperature incubation is not required if RSA is not detected.

Accordingly, the present disclosure provides, in certain embodiments, methods of preventing or reducing RSA of antibodies in formulations. Details of these methods are provided herein. In certain embodiments, the methods relate to preventing or reducing RSA of anti-PDGFR-alpha antibodies in formulations.

Furthermore, the disclosure provides formulations comprising anti-PDGFR-alpha antibodies or antibody fragments. Details of the particular formulations are provided herein. In certain embodiments, the formulations promote preferable non-RSA properties, such as, for example, 1) RSA that does not differ significantly at 2-8° C. versus at room temperature at a given concentration and/or 2) RSA that is not measurable at 2-8° C. by HPSEC at a relevant concentration, such as at least 10 mg/ml and/or 3) RSA that is not measurable at an antibody concentration of at least 4 mg/ml and/or RSA does not vary significantly with concentration. Regardless of the RSA characteristics, it should be understood that the antibodies in the formulation retain their functional attributes, such as the ability to specifically bind to PDGFR-alpha and inhibit the growth of cells that express PDGFR-alpha. Moreover, the disclosure provides methods for reducing or eliminating RSA tendency of an antibody in an initial formulation to achieve one or more of the foregoing RSA characteristics.

As such, the present antibody formulations may be administered to a subject without requiring an extended incubation period after retrieval from storage, thereby simplifying for a healthcare professional the procedure of administering the formulation to a subject. Furthermore, the formulations described herein can contain an antibody (including antibody fragments thereof) at concentrations in the range of about 1 mg/ml to about 100 mg/ml without causing an adverse effect on the biological activities of the antibody due to protein aggregation and/or fragmentation during a prolonged storage. Such stability not only ensures the efficacy of the antibodies but also reduces possible risks of adverse effects in a subject.

Accordingly, the present disclosure provides, in certain embodiments, sucrose-containing antibody formulations that prevent or reduce the RSA tendency of antibodies, in particular, anti-PDGFR-alpha antibody. In addition, provided herein are methods of preventing or reducing RSA of an antibody in an antibody formulation. In certain embodiments, the formulations are liquid formulations. In certain embodiments, the formulations are not suitable for lyophilization. In certain embodiments, the formulations are suitable for lyophilization. In certain embodiments, the antibody in such formulations has favorable RSA characteristics. In certain embodiments, such favorable RSA characteristics are assessed relative to the RSA characteristics of the antibody in an initial formulation.

The formulations of the present disclosure provide a stable ready-to-use preparation of an antibody (including antibody fragments thereof). In a specific embodiment, the formulations of the present disclosure provide a preparation that comprises an anti-PDGFR-alpha antibody.

Without wishing to be bound by theory, the present disclosure is based, in part, on the observation that an anti-PDGFR-alpha antibody in an initial formulation had RSA tendency that influenced the way in which the formulation could be used (see, e.g., Example 1 herein). The monomeric anti-PDGFR-alpha molecules in this initial formulation had a tendency to self-associate, transiently and reversibly, and this RSA was a function of temperature. Specifically, RSA of this antibody in the initial formulation was pronounced at storage conditions of about 2° C. to about 8° C., and was even measurable by HPSEC at 10 mg/ml, as indicated by a shoulder on the leading edge of the monomer peak. In this initial formulation, the shoulder indicative of RSA is still measurable by HPSEC even when the antibody is diluted significantly (e.g., the shoulder was detectable until the antibody was diluted to less than or equal to 4 mg/ml). However, RSA tendency reduced over time and was not detectable following 60 to 90 minutes room temperature equilibrium. As such, extended incubation at room temperature or higher was necessary prior to use of the antibody in this initial formulation. The need for prolonged incubation is a cause for general inconvenience and may potentially introduce a risk for noncompliance.

In certain embodiments, this transient RSA tendency is concentration-dependent and decreases with lower antibody concentrations. For example, the HPSEC shoulder as noted above is detected at 2-8° C. and at a protein concentration of 10 mg/ml. Following dilution to antibody concentrations less than or equal to 4 mg/ml at 2-8° C., the HPSEC shoulder is not observed. Size distribution analyses by AUC at 4° C. also showed less broadening of the product peak at a low antibody concentration. As such, to avoid RSA in this formulation, some antibodies would need to be at a very low concentration (i.e., less than 4 mg/ml). For many therapeutic applications, formulating antibodies at such a low concentration is not practical.

The present disclosure is based, in part, on the surprising discovery that sucrose prevents or reduces the RSA of anti-PDGFR-alpha antibody observed in an initial formulation, and this disclosure is applicable to other antibodies that exhibit RSA as described herein. In certain embodiments, the present description provides methods for preventing or reducing the RSA of an antibody (relative to RSA in an initial formulation), wherein RSA of the antibody in the initial formulation has one or more of the following characteristics: i) RSA is measurable/detected at 2-8° C. at a given antibody concentration, such as 10 mg/ml or at least 10 mg/ml, and said RSA is reduced or eliminated upon room temperature equilibration, ii) RSA is measurable/detected at 2-8° C. at a concentration of greater than 4 mg/ml and said RSA is reduced or eliminated upon dilution to a concentration of 4 mg/ml or less, and/or iii) RSA results from high molecular weight forms (e.g., dimer, trimer, tetramer, pentamer, or higher order oligomers) that reversibly self-associate. The methods of preventing or reducing RSA are particularly suitable for preventing or reducing RSA in antibodies where RSA in an initial formulation has 1, 2, or all 3 of the foregoing characteristics.

As such, the present antibody formulations may be administered to a subject without requiring an extended incubation period after retrieval from storage, thereby simplifying for a healthcare professional the procedure of administering the formulation to a subject. Furthermore, the formulations of the present disclosure can contain an antibody (including antibody fragments thereof) at concentrations in the range of about 1 mg/ml to about 100 mg/ml without causing an adverse effect on the biological activities of the antibody due to RSA, protein aggregation and/or fragmentation during a prolonged storage. Although antibody stability is a property separate from RSA tendency, stability of formulations is important for safety, efficacy, and commercial use. Such stability not only ensures the efficacy of the antibodies but also reduces possible risks of adverse effects in a subject.

Accordingly, the present disclosure provides sucrose-containing antibody formulations that prevents or reduces the RSA tendency of antibodies, in particular, anti-PDGFR-alpha antibody. In addition, provided herein are formulation methodologies of preventing or reducing RSA of an antibody in an antibody formulation.

(ii) Definitions

Before continuing to describe the present invention in further detail, it is to be understood that this invention is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The numbering of amino acids in the variable domain, complementarity determining region (CDRs) and framework regions (FR), of an antibody follow, unless otherwise indicated, the Kabat definition as set forth in Kabat et al. Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

As used herein, the terms "antibody" and "antibodies", also known as immunoglobulins, encompass monoclonal antibodies (including full-length monoclonal antibodies), polyclonal antibodies, multispecific antibodies formed from at least two different epitope binding fragments (e.g., bispecific antibodies), human antibodies, humanized antibodies, camelised antibodies, chimeric antibodies, single-chain Fvs (scFv), Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the disclosure), intrabodies, and epitope-binding fragments of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, etc., or other animals such as birds (e.g. chickens).

As used herein, the term "about" in the context of a given value or range refers to a value or range that is within 20%, preferably within 10%, and more preferably within 5% of the given value or range.

The term "PDGFR-alpha" refers to the platelet derived growth factor tyrosine kinase receptor-alpha. PDGFR-alpha is also known as CD140a and PDGFR-α.

"MabA" refers to a particular, human IgG2 anti-PDGFR-alpha antibody comprising the amino acid sequences set forth in Table 1. Specifically, this antibody comprises the VH and VL set forth in Table 1 (which variable regions include the six CDRs set forth in Table 1). This antibody may also be referred to by its six CDRs as set forth in Table 1 or as an antibody comprising a VH and a VL domain and comprising the six CDRs as set forth in Table 1. This particular human antibody is an example of a PDGFR-alpha antibody that specifically binds to PDGFR-alpha and inhibits growth of cells that express PDGFR-alpha.

The term "neutralizing" when referring to a targeted binding agent such as an antibody relates to the ability of said agent to eliminate, or significantly reduce, the activity of a target antigen. Accordingly, a "neutralizing" anti-PDGFR-alpha antibody is capable of eliminating or significantly reducing the activity of PDGFR-alpha. A neutralizing PDGFR-alpha antibody may, for example, act by blocking the binding of ligand to PDGFR-alpha.

The term "CDR region" or "CDR" is intended to indicate the hypervariable regions of the heavy and light chains of the immunoglobulin as defined by Kabat et al. 1991 (Kabat, E. A. et al. (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

As discussed herein, minor variations in the amino acid sequences of antibodies or immunoglobulin molecules are contemplated as being encompassed by the present antibodies or immunoglobulin molecules, providing that the variations in the amino acid sequence maintain at least 75%, at least 80%, 90%, 95%, or at least 99% sequence identity to the antibodies or immunoglobulin molecules described herein. Variants should retain the desired biological property of the reference antibody. For example, in the context of a PDGFR-alpha antibody, variants should retain the ability to (i) specifically bind PDGFR-alpha and/or (ii) inhibit growth of cells that express PDGFR-alpha. In certain embodiments, a variant is further characterized as: binding the same epitope as a reference antibody and/or competing with the reference antibody for binding to antigen. In certain embodiments, a variant includes 1, 2, 3, 4, 5, 6, 7, 8, 9, or 10 substitutions (including deletions or insertions) relative to a reference antibody. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the antibodies described herein.

An antibody typically inhibits binding of a ligand to a receptor when an excess of antibody reduces the quantity of ligand bound to receptor by at least 50%, 60% or 80%, or greater than about 85% (as measured in an in vitro competitive binding assay).

As used herein the term "monoclonal antibody" refers to an antibody from a substantially homogeneous population of antibodies that specifically bind to the same epitope.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term "specifically binds" refers to antibodies (including antibody fragments) that specifically bind to an antigen. Preferably, antibodies (including antibody fragments) that specifically bind to an antigen do not significantly cross-react with other unrelated antigens. It is understood, however, that antibodies that specifically bind to a particular protein from a given species may also specifically bind to the ortholog of that protein from one or more other species. Such cross-species binding does not alter the characterization of the antibody as specifically binding its antigen. In certain embodiments, an antibody binds specifically to an antigen when it binds to the antigen with substantially higher affinity, for example 100-1000 fold higher affinity, than to any cross-reactive antigen as determined using experimental techniques, such as radioimmunoassays (RIAs) and enzyme-linked immunosorbent assays (ELISAs). See, e.g., Paul, ed., 1989, Fundamental Immunology, 2nd ed., Raven Press, New York at pages 332-336 for a discussion regarding antibody specificity.

As used herein, the term "in combination" refers to the use of more than one therapy (e.g., more than one agent; one or more agents together with one or more additional therapies/therapeutic modalities). The use of the term "in combination" does not restrict the order in which therapies (e.g., agents and/or other therapeutic modalities) are administered to a subject. A first therapy (e.g., a first agent and/or other therapeutic modality) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks, after) the administration of a second therapy (e.g., a second agent and/or other therapeutic modality) to a subject. By way of example, "other therapeutic modalities" include, but are not limited to, surgery, radiation therapy, dialysis, stem cell transplant, ventilatory support, diet, physical therapy, etc.

The term "excipient" as used herein refers to an inert substance which is used as a diluent, vehicle, preservative, binder or stabilizing agent in a formulation which imparts a beneficial physical property to a formulation, such as increased protein stability, increased protein solubility, and decreased viscosity. Examples of excipients include, but are not limited to, proteins (e.g., serum albumin), amino acids (e.g., aspartic acid, glutamic acid, lysine, arginine, glycine and histidine), surfactants (e.g., SDS, polysorbate and nonionic surfactant), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18.sup.th ed., Mack Publishing Co., Easton, Pa.), which is incorporated herein in its entirety.

The term "polyol" as used herein refers to a sugar that contains many —OH groups compared to a normal saccharide.

"Reversible self-association tendency", "reversible self-association characteristics", "RSA", or "reversible self-association" are used interchangeably, and refer to the transient self-associating property of a protein or antibody molecule with another molecule or group of molecules of the protein or antibody (i.e., intermolecular interaction). RSA is usually concentration dependent and increases with the protein concentration. RSA, described herein, can also be temperature dependent and may be observed at low temperatures, whereas dissociation is favored as the temperature is increased.

"Measurable RSA" or "measurable RSA tendency" is used interchangeably to refer to RSA that can be detected using, for example, HPSEC or AUC. RSA measurable by HPSEC may also be measurable by other orthogonal methods.

"Preventing" or "eliminating" refers to RSA that is undetectable or non-measurable when examined by the methods described herein (e.g., HPSEC). Additionally, the terms also apply when RSA is substantially the same when compared to a formulation wherein RSA is absent (e.g., a control sample that does not exhibit RSA).

"High molecular weight forms" or "higher order forms" refer to any protein species in a given formulation other than a monomer (e.g., dimers, trimers, tetramers, pentamers, etc.) in a transient or permanent state (i.e., a reversible or non-reversible higher order form).

"Non-RSA" refers to the absence of RSA, or RSA that is undetectable or non-measurable when examined by the methods described herein (e.g., HPSEC).

"Non-self-associated monomers" refers to antibodies or functional fragments that are present in a formulation as a monomer (a Y-shaped antibody molecule), rather than, for example, as a dimer (two Y-shaped molecules), trimer (three Y shaped molecules), fragment, etc.

"Stable" and "stability" refer to maintenance of the starting level of purity of a formulation over a period of time. In other words, if a formulation is 99% pure with respect to a given antibody species at time 0, stability is a measure of how well and for how long the formulation retains substantially this level of purity (e.g., without formation of other species, such as fragmented portions or aggregates of the pure species). A formulation is stable if the level of purity does not decrease substantially when stored at approximately 2-8° C. over a given period of time. Preferably, a stable formulation is one in which stability does not decrease substantially at storage conditions over a period of at least 2 years. Similarly, stability is measured by the level of purity of a formulation, as determined by, e.g., HPSEC, when stored at approximately 2-8° C. over a given period of time. By "not decrease substantially", is meant that the level of purity of the formulation changes by less than 1% per year, less than 0.75% per year, less than 0.5% or less than 0.4% per year over a given period of time. Stability can similarly be assessed at other temperatures.

(iii) Antibodies

The present disclosure provides methods for reducing RSA tendency of antibodies and antibody fragments in formulations. Additionally, the present disclosure provides particular formulations comprising anti-PDGFR-alpha antibodies and antibody fragments that specifically bind to PDGFR-alpha and inhibit growth of cells that express PDGFR-alpha. Such formulations may be used, for example, therapeutically and diagnostically. In certain embodiments, formulations of the disclosure have reduced RSA tendency.

Before discussing the particular formulations and/or the more general methods for reducing RSA, a brief description of antibodies is provided. Unless otherwise specified, this general discussion of antibodies and antibody fragments applies to any antibody or antibody fragment, such as an antibody or antibody fragment for which RSA may be reduced by increasing sucrose in the formulation.

Antibodies (including antibody fragments) that specifically bind to an antigen, e.g., PDGFR-alpha, can be produced by any method known in the art for the synthesis of antibodies, in particular, by chemical synthesis or by recombinant expression techniques.

Antibody Structure

The basic native antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site. In the context of a full length antibody, the basic unit of a monomeric IgG antibody molecule is often depicted as a Y.

Thus, an intact native antibody has two binding sites. Examples of antibodies in which the two binding sites are not the same include bifunctional or bispecific antibodies.

Native antibody chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

In certain circumstances there are advantages to using antibody fragments. For example, without wishing to be bound by theory, the use of antibody fragments may lead to improved access to solid tumors and/or may allow for rapid clearance.

Various techniques have been developed for the production of antibody fragments. Traditionally, these fragments were derived via proteolytic digestion of intact antibodies (see, e.g., Morimoto et al., J Biochem Biophys. Method. 24:107-117 (1992); and Brennan et al., Science 229:81 (1985)). However, these fragments can now be produced directly by recombinant host cells. Fab, Fv and scFv antibody fragments can be expressed in and secreted from cells, such as $E.\ coli$, thus allowing the facile production of large amounts of these fragments. Antibody fragments can be isolated from, e.g., antibody phage libraries. Alternatively, Fab'-SH fragments can be directly recovered from $E.\ coli$ and chemically coupled to form $F(ab')_2$ fragments (Carter et al., Bio/Technology 10:163-167 (1992)). According to another approach, $F(ab')_2$ fragments can be isolated directly from recombinant host cell culture. Fab and $F(ab')_2$ with increased in vivo half-life is described in U.S. Pat. No. 5,869,046. In other embodiments, the antibody of choice is a single chain Fv fragment (scFv). See WO 93/16185; U.S. Pat. Nos. 5,571,894 and 5,587,458. The antibody fragment may also be a "linear antibody", e.g., as described in U.S. Pat. No. 5,641,870. Such linear antibody fragments may be monospecific or bispecific.

A VH domain may be paired with a VL domain to provide an antibody antigen-binding site, although a VH or VL domain alone may be used to bind antigen. The VH domain may be paired with the VL domain, so that an antibody antigen-binding site is formed comprising both the VH and VL domains.

Human Antibodies and Humanization of Antibodies

In certain embodiments, antibodies and antibody fragments for use in the claimed methods and formulations are human or humanized. In other embodiments, antibodies or antibody fragments are murine. Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. Nature Genetics 15:146-156 (1997) and Green and Jakobovits J. Exp. Med. 188:483-495 (1998). The XenoMouse® strains are available from Amgen, Inc. (Fremont, Calif., U.S.A).

Such mice, then, are capable of producing human immunoglobulin molecules and antibodies and are deficient in the production of murine immunoglobulin molecules and antibodies. Technologies utilized for achieving the same are disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. Nature Genetics 15:146-156 (1997), the disclosure of which is hereby incorporated by reference.

The production of the XenoMouse® strains of mice is further discussed and delineated in U.S. patent application Ser. Nos. 07/466,008, filed Jan. 12, 1990, Ser. No. 07/610, 515, filed Nov. 8, 1990, Ser. No. 07/919,297, filed Jul. 24, 1992, Ser. No. 07/922,649, filed Jul. 30, 1992, Ser. No.

08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. Nos. 07/574,748, filed Aug. 29, 1990, Ser. No. 07/575, 962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KMTM-mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

Note that the foregoing techniques are merely exemplary of methods of generating human antibodies. Moreover, murine antibodies can be generated using, for example, standard hybridoma techniques. Regardless of how a particular antibody is initially made, once the amino acid sequence of the antibody is identified, the antibody can readily be produced recombinantly. For example, antibodies and antibody fragments, whether murine, humanized, human, etc., can be expressed in cells and purified from such cells in culture. Exemplary cells that can be used to recombinantly express antibodies and antibody fragments include, but are not limited to, CHO cells, COS cells, yeast cells, and bacterial cells. This is described below in greater detail.

Provided in Table 1 are the sequences for an exemplary PDGFR alpha antibody used in the context of the claimed compositions and methods. However, in other embodiments, the formulations and/or methods of the disclosure utilize other PDGFR alpha antibodies, such as antibodies that bind the same epitope as an antibody having any of the sequences set forth in Table 1 or antibodies that compete with binding for antigen with an antibody having any of the sequences set forth in Table 1.

Competition between antibodies may be assayed easily in vitro, for example using ELISA and/or by tagging a specific reporter molecule to one binding member which can be detected in the presence of one or more other untagged antibodies, to enable identification of antibodies which bind the same epitope or an overlapping epitope. Such methods are readily known to one of ordinary skill in the art, and are described in more detail herein. Thus, a further aspect of the present disclosure provides an antigen binding site comprising a human antibody antigen-binding site that competes with an antibody molecule, for example especially an antibody molecule comprising a VH and/or VL domain, CDR e.g. HCDR3 or set of CDRs of the parent antibody or any of antibodies disclosed herein that bind to PDGFR-alpha.

In certain embodiments, antibodies or antibody fragments may be tagged, labeled, or fused with another moiety. For example, an antibody or antibody fragment may be labeled with a fluorescent, metal, or radioactive moiety to facilitate detection, such as in a diagnostic or imaging context. By way of further example, an antibody or antibody fragment may be pegylated to improve in vivo pharmcokinetic properties. By way of further example, an antibody or antibody fragment may be appended with all or a portion of HSA to improve serum half life. By way of additional example, the antibody or antibody fragment may include a myc or HA tag to facilitate purification and/or detection. The foregoing are merely exemplary.

Preparation of Antibodies

In general, antibodies can be produced by methods known in the art, such as hybridoma technology (mouse or human), phage display, and the like. Once a desired antibody (e.g., an antibody having the functional characteristics desired) is identified, continued preparation can be done using a hybridoma and/or by recombinantly expressing nucleotide sequence encoding the antibody in cells in culture.

As will be appreciated, antibodies or antibody fragments, such as anti-PDGFR-alpha antibodies that are formulated in the context of the present disclosure, can be expressed in cell lines other than hybridoma cell lines. Sequences encoding particular antibodies can be used to transform a suitable mammalian host cell or a non-mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines.

Once antibodies or antibody fragments are produced, they can be formulated as described herein and/or they can be used in the methods described herein. By way of example, anti-PDGFR-alpha antibodies are useful in the detection of PDGFR-alpha in patient samples and accordingly are useful as diagnostics for disease states, such as the neoplastic conditions described herein. In certain embodiments, the antibodies are formulated in a manner that helps minimize RSA tendency, and such a formulation is used in a diagnostic method. In certain embodiments, the formulation used in a diagnostic method does not have measurable RSA tendency when assessed by HPSEC at approximately 2-8° C. and at a given relevant concentration, such as about 10 mg/ml.

By way of further example, based on their ability to inhibit tumor growth, anti-PDGFR-alpha antibodies have therapeutic effects in treating symptoms and conditions resulting from PDGFR-alpha expression. Once antibodies or antibody fragments are produced, they can be formulated as described herein and/or they can be used in the methods described herein. In specific embodiments, the antibodies and methods herein relate to the treatment of neoplastic conditions, such as neoplastic conditions resulting from PDGFR-alpha induced tumor growth. Further embodiments involve using the antibodies and methods described herein to treat neoplastic diseases, such as cancers including, lung cancer, ovarian cancer, prostate cancer, colon cancer, glioblastoma multiforme, melanoma, and gastrointestinal stromal tumor (GIST), renal cell carcinoma, hepatocellular carcinoma, and the like.

In certain embodiments, the antibodies are formulated in a manner that helps minimize RSA tendency. Such formulations may be used, for example, in therapeutic or diagnostic methods. In certain embodiments, the formulation used in a therapeutic method does not have measurable RSA tendency when assessed by HPSEC at approximately 2-8° C. and at concentrations of greater than 4 mg/ml, e.g., at least 10 mg/ml, at least 20 mg/ml, or at least 50 mg/ml, or at least 100 mg/ml.

PDGFR-Alpha Antibodies

In certain embodiments, anti-PDGFR-alpha antibodies specifically bind to PDGFR-alpha and inhibit the growth of cells that express PDGFR-alpha. In certain embodiments, said antibodies are neutralizing antibodies that, for example, bind to PDGFR-alpha and prevent binding of ligand to PDGFR-alpha. In certain embodiments, the antibody is a full length antibody, such as a full length IgG antibody. In certain embodiments, the antibody is an IgG2 or IgG4 antibody. In other embodiments, the antibody is an IgG1 antibody. In other embodiments, the antibody is an antibody fragment that specifically binds to PDGFR-alpha and inhibits the growth of cells that express PDGFR-alpha. Any of these antibodies and antibody fragments are, in certain embodiments, human antibodies.

Exemplary antibodies specifically bind to PDGFR-alpha and inhibit growth of cells that express PDGFR-alpha. Such antibodies can be characterized based on those functions and/or sequence. Such antibodies can also be characterized based on one or more other functional features, such as $K_D$ (e.g., the affinity for antigen). By way of further example, such antibodies can be characterized based on cross-reactivity with PDGFR-alpha from species other than human. Thus, in certain embodiments, an exemplary antibody or antibody fragment specifically binds to human PDGFR-alpha and also binds specifically to PDGFR-alpha from one or more other species, such as mouse, rat, or cynomolgus. In certain embodiments, antibodies or antibody fragments that specifically bind to PDGFR-alpha and inhibit growth of cells that express PDGFR-alpha are high affinity antibodies, such as antibodies having a $K_D$ of from about $10^{-6}$ through about $10^{-12}$ M or better (e.g., lower $K_D$ indicates a higher affinity antibody). In other embodiments, such antibodies have a $K_D$ of less than about 500, 400, 300, 200 or 100 picomolar (pM) and inhibit growth of cells that express PDGFR-alpha. In certain embodiments, such antibodies inhibit tumor growth. In some embodiments, the antibodies bind PDGFR-alpha with a $K_D$ of less than about 75, 60, 50, 40, 30, 25, 20, 10, or 5 pM and inhibit growth of cells that express PDGFR-alpha. In certain embodiments, such antibodies inhibit tumor growth.

Affinity can be measured by solid phase or solution phase technques, such as against cells using FACS-based affinity measurement techniques. Affinity can also be measured by using surface plasmon resonance assays using a BIACORE™-2000 or a BIACORE™-3000 (BIAcore, Inc., Piscataway, N.J.). For example, using surface plasmon resonance assays at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 110 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Regardless of the particular experimental parameters, surface plasmon resonance assays can be used to measure $K_D$, Ka, as well as $k_{on}$ and $k_{off}$. Association rates ($k_{on}$) and dissociation rates ($k_{off}$) are calculated using a simple one-to-one Langmuir binding model (BIACORE™ Evaluation Software version 3.2) by simultaneously fitting the association and dissociation sensorgram.

Exemplary antibodies and antibody fragments that specifically bind to PDGFR-alpha and inhibit growth of cells that express PDGFR-alpha are provided in U.S. patent application Ser. No. 11/833,473 (also referred to herein as the "473 application"), which is incorporated by reference in its entirety. Briefly, the '473 application provides various antibodies, specifically human antibodies that specifically bind to PDGFR-alpha, as described in that application. In certain embodiments, the present disclosure contemplates that any such anti-PDGFR-alpha antibodies or antibody fragments that specifically bind to PDGFR-alpha and inhibit growth of cells that express PDGFR-alpha can be formulated as described in this application and/or can be used in the methods and kits described in this application. Embodiments of the disclosure include specific anti-PDGFR-alpha antibodies or antibody fragments for which sequence information is provided in Table 1. Table 1 provides sequence information for the variable regions of the heavy and light chains, as well as sequence information for each of the CDRs (which are a subset of the sequences of the variable regions) for a particular human PDGFR-alpha antibody.

Briefly, anti-PDGFR-alpha antibodies described in U.S. application Ser. No. 11/833,473 were prepared through the utilization of the XenoMouse® technology, as described in said application, which is incorporated herein by reference in its entirety. Briefly, XenoMouse® lines of mice are immunized with an antigen of interest (e.g. PDGFR-alpha), lymphatic cells (such as B-cells) are recovered from the hyperimmunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. The particular antibody used in the formulations described in the examples is a human, IgG2 antibody that was initially produced using this method and described in application Ser. No. 11/833,473. Table 1 provides sequence information for the variable regions of the heavy and light chains, as well as sequence information for each of the CDRs (which are a subset of the sequences of the variable regions) for the antibody used in the formulations described in the examples. Additional information regarding other human antibodies that specifically bind to PDGFR-alpha can be found in U.S. Ser. No. 11/833,473, which is incorporated by reference in its entirety.

TABLE 1

Sequence of anti-PDGFR-alpha antibody

| SEQ ID NO: | Sequence description | Sequence |
|---|---|---|
| 1 | Anti-PDGFR-alpha $V_H$ | QVQLVESGGGLVKPGGSLRL SCAASGFTFSDYYMNWIRQA PGKGLEWVSYISSSGSIIYY ADSVKGRFTISRDNAKNSLY LQMNSLRAEDTAVYYCAREG RIAARGMDVWGQGTTVTVSS |
| 2 | Anti-PDGFR-alpha $V_L$ | DIQMTQSPSSLSASVGDRVT ITCRPSQSFSRYINWYQQKP GKAPKLLIYAASSLVGGVPS RFSGSGSGTDFTLTISSLQP EDFATYYCQQTYSNPPITFG QGTRLEIK |
| 3 | Anti-PDGFR-alpha $V_H$ CDR1 | GFTFSDYYMN |
| 4 | Anti-PDGFR-alpha $V_H$ CDR2 | YISSSGSIIYYADSVKG |
| 5 | Anti-PDGFR-alpha $V_H$ CDR3 | EGRIAARGMDV |

TABLE 1-continued

Sequence of anti-PDGFR-alpha antibody

| SEQ ID NO: | Sequence description | Sequence |
|---|---|---|
| 6 | Anti-PDGFR-alpha $V_L$ CDR1 | RPSQSFSRYIN |
| 7 | Anti-PDGFR-alpha $V_L$ CDR2 | AASSLVG |
| 8 | Anti-PDGFR-alpha $V_L$ CDR3 | QQTYSNPPIT |

As detailed above, the disclosure contemplates formulations comprising anti-PDGFR-alpha antibodies and antibody fragments that specifically bind to PDGFR-alpha, as well as methods of using such antibodies, antibody fragments and formulations. In certain embodiments, an anti-PDGFR-alpha antibody or antibody fragment for use in the claimed formulations or methods comprises a heavy chain polypeptide comprising the amino acid sequence of SEQ ID NO: 1. In certain embodiments, a PDGFR-alpha antibody or antibody fragment for use in the claimed formulations or methods comprises a light chain polypeptide comprising the amino acid sequence of SEQ ID NO: 2. In certain embodiments, a PDGFR-alpha antibody or antibody fragment for use in the claimed formulations or methods comprises a heavy chain polypeptide comprising the amino acid sequence of SEQ ID NO: 1 and a light chain polypeptide comprising the amino acid sequence of SEQ ID NO: 2. In other embodiments, a PDGFR-alpha antibody or antibody fragment for use in the claimed formulations or methods comprises at least one CDR set forth in Table 1. In other embodiments, an anti-PDGFR-alpha antibody or antibody fragment for use in the claimed formulations or methods comprises at least two, at least three, at least four, or at least five of the CDRs set forth in Table 1. In other embodiments, an anti-PDGFR-alpha antibody or antibody fragment for use in the claimed formulations or methods comprises all six CDRs set forth in Table 1. In other embodiments, an anti-PDGFR-alpha antibody or antibody fragment for use in the claimed formulations or methods binds to the same epitope as an antibody or antibody fragment having any one or more of the sequence characteristics set forth in this paragraph. By way of non-limiting example, such an antibody or antibody fragment specifically binds to PDGFR-alpha and binds to the same epitope as an antibody or antibody fragment comprising the six CDRs set forth in Table 1. In other embodiments, an anti-PDGFR-alpha antibody or antibody fragment for use in the claimed formulations or methods competes for binding to PDGFR-alpha with an antibody or antibody fragment having any one or more of the sequence characteristics set forth in this paragraph. By way of non-limiting example, such an antibody or antibody fragment specifically binds to PDGFR-alpha and competes for binding to PDGFR-alpha with an antibody or antibody fragment comprising the six CDRs set forth in Table 1. For all of the foregoing, it is understood that the anti-PDGFR-alpha antibodies and antibody fragments specifically bind to PDGFR-alpha. In certain embodiments, the anti-PDGFR-alpha antibodies or antibody fragments specifically bind to PDGFR-alpha and inhibit growth of cells that express PDGFR-alpha. In certain embodiments, any of the foregoing antibodies or antibody fragments are formulated in a sucrose-containing formulation with preferable RSA characteristics, such as, undetectable RSA relative to a non-sucrose-containing formulation; RSA that is not measurable at about 2-8° C. by HPSEC when assessed at a relevant concentration, e.g., at least 10 mg/ml; and/or RSA that is not measurable at 2-8° C. and which is not temperature dependent (e.g., RSA is substantially similar at 2-8° C. versus 23-27° C.).

Preparation of Formulation

The present disclosure provides methods for preparing formulations of antibodies or derivatives, analogues, or fragments thereof, as well as formulations comprising sucrose. In certain embodiments, the formulations comprise antibodies or antibody fragments that specifically bind to PDGFR-alpha and inhibit growth of cells that express PDGFR-alpha. The disclosure contemplates that, in certain embodiments, the formulation comprises any of the PDGFR-alpha antibodies that specifically bind to PDGFR-alpha disclosed herein or disclosed in application Ser. No. 11/833,473. In certain embodiments, the formulations are liquid formulations. In certain embodiments, the formulations are suitable for lyophilization. In certain other embodiments, the formulations are not suitable for lyophilization. In some embodiments, the methods described herein are specific to liquid formulations. In certain embodiments, formulations of the disclosure prevent or reduce the RSA in formulations or are formulations in which RSA is not measurable by HPSEC when assessed at a relevant concentration, such as greater than 4 mg/ml, e.g., at least 10 mg/ml, at least 15 mg/ml, at least 20 mg/ml, at least 50 mg/ml or at least 100 mg/ml.

The methods for preparing formulations as described herein may comprise: purifying the antibody (including antibody fragment thereof) from conditioned medium (either single lots or pooled lots of medium) and concentrating a fraction of the purified antibody (including antibody fragment thereof).

The formulations of the present disclosure may comprise an aqueous carrier, sucrose, sodium-acetate buffer, polysorbate 80, and an antibody or antibody fragment that specifically binds to PDGFR-alpha and inhibits the growth of cells that express PDGFR-alpha. The concentration and/or proportions of each of these components of the formulation is detailed below. It should be understood that the disclosure contemplates formulations comprising any combination of the specific concentrations of components set forth below. Additionally, for formulations that may optionally comprise other excipients (the concentrations of which are provided below), it should be understood that the description contemplates formulations comprising any combination of these features. Moreover, the disclosure contemplates that, in certain embodiments, the formulation may include a different acetate-salt buffer in addition to or instead of sodium-acetate buffer.

In certain embodiments, the antibody or antibody fragment is present in the formulation at a concentration of about 1 mg/ml to about 100 mg/ml. In other embodiments, the antibody or antibody fragment is present at a concentration of about 1 mg/ml to about 70 mg/ml. In other embodiments, the antibody or antibody fragment is present at a concentration of about 10 mg/ml to about 50 mg/ml or about 20 mg/ml to about 50 mg/ml. In other embodiments, the antibody or antibody fragment is present at a concentration of about 10 mg/ml to about 50 mg/ml. In other embodiments, the antibody or fragment is present at a concentration of about 1, 5, 10, 15, 20, 25, 30, 35, 40, 45, 50, 55, 60, 65, 70, or about 75, or about 100 mg/ml. In certain embodiments, the antibody or fragment is present at a concentration of about 20 mg/ml or about 50 mg/ml.

In certain embodiments, the formulation optionally comprises sodium chloride. In one embodiment, the formulations of the disclosure do not comprise other ingredients except for water or suitable solvents. In other words, in certain embodiments, the formulation consists of aqueous carrier, sucrose, sodium-acetate buffer, polysorbate 80 (PS80), and an antibody or antibody fragment that specifically binds to PDGFR-alpha and inhibits the growth of cells that express PDGFR-alpha. In another embodiment, the water is distilled. In a specific embodiment, the antibody that immunospecifically binds to PDGFR-alpha which is included in the formulation of the disclosure is an antibody (including antibody fragment thereof) comprising one or more of the VH CDRs and/or one or more of the VL CDRs listed in Table 1, supra.

In certain embodiments, the formulations of the present disclosure provide antibody formulations which are substantially free of crystalline bulking agents. In a specific embodiment, antibody formulations are homogeneous. In a preferred embodiment, antibody formulations of the disclosure are sterile and/or pyrogen-free.

The formulations of the present disclosure comprise, in part, sucrose at a concentration (weight/volume) ranging from about 4% to about 20%. In certain embodiments, the formulation comprises about 4% to about 15% sucrose, about 4% to about 12% sucrose, about 5% to about 12% sucrose, or about 6% to about 12% sucrose. In other embodiments, the formulation comprises about 5% to about 10% sucrose or about 6% to about 10% sucrose. All of the foregoing are provided as w/v. In other embodiments, the formulation comprises about 4%, about 5%, about 6%, about 7%, about 8%, or about 9% (w/v) sucrose. In other embodiments, the formulation comprises about 10% (w/v) sucrose. In other embodiments, the formulation comprises about 11%, about 12%, about 13%, about 14% or about 15% (w/v) sucrose. In other embodiments, the formulation comprises about 16%, about 17%, about 18%, or about 20% (w/v) sucrose.

The pH of the formulation generally should not be equal to the isoelectric point of the particular antibody (including antibody fragment thereof) and may range from about 4.0 to about 6.0, about 5.0 to about 6.0, about 5.2 to about 6.0, or about 5.5 to about 6.0. In certain embodiments, the pH of the formulation is about 5.5. In certain embodiments, the pH of the formulation is about 5.0 or about 5.2 or about 6.0.

In addition to sucrose and an antibody or antibody fragment that specifically binds to PDGFR-alpha, the formulations of the present disclosure may further comprise polysorbate 80 (PS80) at about (weight/volume) 0.01%, about 0.02%, 0.03%, 0.04%, 0.05%, 0.06%, about 0.07%, 0.08%, 0.09%, or about 0.1%. In certain embodiments, the formulations comprise polysorbate 80 at about 0.05% (w/v). In certain embodiments, the formulations of the present disclosure comprise about 0.01% to about 0.07% (w/v) PS80, about 0.01% to about 0.05%, about 0.02% to about 0.06%, or about 0.03% to about 0.05% (weight/volume) PS80. In certain embodiments, polysorbate 20 may be used alternatively or in addition to PS80. Polysorbate 20 may be used over a similar range of concentrations.

In certain embodiments, the sodium-acetate buffer in the formulation is about 25 mM to about 150 mM; about 25 mM to about 100 mM; about 40 mM to about 100 mM; about 50 mM to about 100 mM; or about 50 to about 75 mM. In certain embodiments, the sodium-acetate buffer in the formulation is about 25, 30, 40, 45, 50, 55, 60, 70, 75, 80, 90, or about 100 mM. In certain embodiments, the sodium-acetate buffer in the formulation is about 100, 110, 125, or about 150 mM. In certain embodiments, the formulation includes a different acetate-salt buffer in addition to or instead of sodium-acetate buffer. For example, when a different acetate-salt buffer is used instead of sodium-acetate, such an acetate-salt buffer can be used at any of the foregoing concentrations recited for an exemplary sodium-acetate buffer. By way of further example, when a combination of acetate-salt buffers are used, such combination may be in any ratio with the total concentration being as those recited for an exemplary sodium-acetate buffer.

In certain embodiments, the aqueous carrier is water, such as sterile water for injection.

In certain specific embodiments, the formulation comprises, in addition to antibody, (or, alternatively, consists of) an aqueous carrier, 50 mM sodium-acetate, 10% (w/v) sucrose, 0.05% (w/v) PS80, pH 5.5. In another embodiment, the formulation comprises, in addition to antibody, (or, alternatively, consists of) an aqueous carrier, 25 mM sodium-acetate, 50 mM sodium chloride, 6% (w/v) sucrose, 0.03% (w/v) PS80, pH 5.5. In another embodiment, the formulation comprises, in addition to antibody, (or, alternatively, consists of) an aqueous carrier, 50 mM Na-acetate, 50 mM sodium chloride, 6% (w/v) sucrose, 0.03% (w/v) PS80, pH 5.5. In another embodiment, the formulation comprises, in addition to antibody, (or, alternatively, consists of) an aqueous carrier, 25 mM histidine, 50 mM sodium chloride, 6% (w/v) sucrose, 0.03% (w/v) PS80, pH 5.5. In another embodiment, the formulation comprises, in addition to antibody, (or, alternatively, consists of) an aqueous carrier, 25 mM sodium-acetate, 50 mM sodium chloride, 10% (w/v) sucrose, 0.05% (w/v) PS80, pH 5.5. In any of the specific formulations, the antibody concentration may be 20 mg/ml or 50 mg/ml.

In certain embodiments, the formulations include one or more additional components, such as excipients. In certain embodiments, the formulations do not include any additional components, such as excipients.

In certain embodiments, the formulations of the present disclosure may further be buffered by histidine. The concentration of histidine which is included in the formulations of the description may range from 1 mM to 100 mM, 5 mM to 50 mM, and 10 mM to about 25 mM. In a specific embodiment, the concentration of histidine which is included in the formulations of the disclosure is 5 mM, 10 mM, 15 mM, 20 mM, 25 mM, 30 mM, 35 mM, 40 mM, 45 mM, or 50 mM. Histidine can be in the form of L-histidine, D-histidine, or a mixture thereof, but L-histidine is the most preferable. Histidine can be also in the form of hydrates. Histidine may be used in a form of pharmaceutically acceptable salt, such as hydrochloride (e.g., monohydrochloride and dihydrochloride), hydrobromide, sulfate, acetate, etc. The purity of histidine should be at least 98%, preferably at least 99%, and most preferably at least 99.5%. As used herein, the term "purity" in the context of histidine refers to chemical purity of histidine as understood in the art, e.g., as described in The Merck Index, 13$^{th}$ ed., O'Neil et al. ed. (Merck & Co., 2001). In certain embodiments, the formulation does not include histidine.

The formulations may further comprise glycine at a concentration of less than 150 mM, less than 100 mM, less than 75 mM, less than 50 mM, less than 10 mM, less than 3.0 mM, or less than 2.0 mM. The amount of glycine in the formulation should not cause a significant buffering in order to avoid antibody precipitation at its isoelectric point. In certain embodiments, the formulation does not include glycine.

In other embodiments, the formulations of the present disclosure may further comprise NaCl. The concentration of NaCl which is included in the formulations ranges from 10 mM, 20 mM, 30 mM, 40 mM, 50 mM, 60 mM, or 70 mM. However, in other embodiments, the formulation specifically does not include additional NaCl.

Optionally, the formulations may further comprise other excipients, such as saccharides (e.g., mannose, trehalose, etc.), polyols (e.g., mannitol, sorbitol, etc.), and detergents. In one embodiment, the other excipient is a saccharide. In a specific embodiment, the saccharide is trehalose, which is at a concentration ranging from between about 1% to about 15%, about 5% to about 12%, and about 8% to 10% of the formulation. In another embodiment, the trehalose is at a concentration of 1%, 2%, 3%, 4%, 5%, 6%, 8%, or 10% of the formulation. In another embodiment, an excipient is a polyol. Preferably, however, the formulations do not contain mannitol. In certain embodiments, the formulation does not include any additional saccharide, other than sucrose. In certain embodiments, the formulation does not include any polyol. In certain embodiments, the formulation does not include any saccharide, other than sucrose, and does not include any polyol. In certain embodiments of any of the foregoing, the formulation does not include any additional detergent, other than PS80.

For any of the foregoing, it should be noted that the antibody or antibody fragment in the formulation retains the desired biological activity. For example, a PDGFR-alpha antibody retains the ability to specifically bind to PDGFR-alpha and inhibit growth of cells that express PDGFR-alpha.

In certain embodiments, the formulations of the present disclosure exhibit stability at the temperature range of 38-42° C. for at least 15 days and, in some embodiments, not more than 1 month. Additionally or alternatively, in certain embodiments, the formulations are stable at the temperature range of 20° C.-24° C. or 23° C.-27° C. for at least 6 months and/or at the temperature range of 2° C.-8° C. for at least 6 months, at least 1 year, at least 1.5 years, at least 2 years, at least 2.5 years, at least 3 years or at least 4 years. Additionally or alternatively, in certain embodiments, the formulations are stable at the temperature of −20° C. for at least 2 years, at least 3 years, at least 4 years, or at least 5 years. Stability may be assessed, for example, by high performance size exclusion chromatography (HPSEC). In certain embodiments, stability can be assessed by maintenance of a level of purity over time. For example, in certain embodiments, formulations of the present disclosure have less than 1%, less than 0.8%, less than 0.75%, less than 0.7%, less than 0.6%, less than 0.5%, or even less than 0.4% decrease in purity/year when stored at 2-8° C., as determined by HPSEC. In one embodiment, formulations of the present disclosure have a shelf-life of greater than 6 months, greater than 1 year, or greater than 18 months with less than 0.2% purity loss over 6 months at 2-8° C. as determined by HPSEC, which monitors the presence or absence of fragments and/or aggregate species.

In certain embodiments, the formulations of the present disclosure promote low to undetectable levels of aggregation and/or fragmentation, as defined herein, after the storage for the defined periods as set forth above. Preferably, no more than 5%, no more than 4%, no more than 3%, no more than 2%, no more than 1%, and most preferably no more than 0.5% of the antibody (including antibody fragment thereof) forms fragment or aggregate (reversible or non-reversible) forms as measured by HPSEC, after the storage for the defined periods as set forth above. Furthermore, formulations of the present disclosure render almost no loss in biological activities of the antibody (including antibody fragment thereof) during the prolonged storage under the condition described above, as assessed by various immunological assays including, for example, enzyme-linked immunosorbent assay (ELISA) and radioimmunoassay to measure the ability of the antibody (including antibody fragment thereof) to immunospecifically bind to PDGFR-alpha. The formulations of the present disclosure promote, after the storage for the above-defined periods, more than 80%, more than 85%, more than 90%, more than 95%, more than 98%, more than 99%, more than 99.5%, more than 99.8%, or more than 99.9% retention of the initial biological activities (e.g., the ability to bind to PDGFR-alpha) of the formulation prior to the storage. In some embodiments, the formulations of the present disclosure promote, after the storage for the above-defined periods, at least 80%, at least 85%, at least 90%, at least 95%, at least 98%, at least 99%, at least 99.5%, at least 99.8%, or at least 99.9% retention of the biological activity (e.g., the ability to bind to PDGFR-alpha) compared to a reference antibody representing the antibody prior to the storage.

In certain embodiments, the formulations have preferable non-RSA properties, as described herein. In certain embodiments, RSA of antibodies in the formulation is not measurable by HPSEC at 2-8° C. when assessed at a relevant concentration, such as greater than 4 mg/ml, e.g., at least 10 mg/ml. Additionally or alternatively, RSA of antibodies in the formulation is substantially similar at 2-8° C. and at 23-27° C., when measured by one or both of HPSEC and AUC at a relevant concentration. We note that when evaluating whether RSA has been reduced or eliminated, it is important to perform the HPSEC analysis at a relevant concentration, such as 10 mg/ml or 20 mg/ml. This is important because the measurement of RSA tendency can be falsely skewed by diluting an antibody to a sufficiently low concentration. Thus, an assessment that RSA is not detectable by HPSEC when measured at a concentration of, for example, 1-4 mg/ml, may not be an accurate indicator of RSA characteristics of the antibody such as when evaluated at a concentration that is closer to the concentration at which the antibody will be stored and/or used. Accordingly, to properly evaluate whether RSA has, in fact, been eliminated and is not measurable by HPSEC at 2-8° C., it is important to conduct the analysis at an appropriate concentration, such as at least about 10 mg/ml or about 10 mg/ml.

In certain embodiments, the formulations have preferable non-RSA properties such that at least 95% of the antibodies in the formulation are present in non-self-associating, monomeric form, when assessed at 2-8° C. In other embodiments, at least about 96%, 97%, 98%, or 99% of the antibodies in the formulation are present in non-self-associating, monomeric form, when assessed at 2-8° C. In other embodiments, about 95%, 96%, 97%, 98%, or about 99% of the antibodies in the formulation are present in non-self-associating, monomeric form, when assessed at 2-8° C.

The formulations of the present disclosure can be prepared as unit dosage forms. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of an antibody or antibody fragment that immunospecifically binds to PDGFR-alpha ranging from about 1 mg/ml to about 100 mg/ml, about 1 mg/ml to about 100 mg/ml, about 5 mg/ml to about 100 mg/ml, about 10 mg/ml to about 100 mg/ml, about 15 mg/ml to about 70 mg/ml, or about 20 mg/ml to about 50 mg/ml. If necessary, these preparations can be adjusted to a desired concentration by adding a sterile diluent to each vial.

The formulations of the present disclosure may be sterilized by various sterilization methods, including sterile filtration. In certain embodiments, the antibody formulation is filter-sterilized, for example, with a presterilized 0.2 micron filter. Sterilized formulations of the present disclosure may be administered to a subject to prevent, treat or ameliorate a disease or disorder and/or may be used in a diagnostic method.

Initial Characterization of the RSA Tendency of MabA in an Initial Formulation

RSA tendency of MabA in an initial, non-sucrose containing formulation was evaluated at an antibody concentration of 10 mg/ml. In addition to antibody, the initial formulation contained, in water, 50 mM sodium-acetate, 100 mM NaCl, 0.01% (w/v) PS80, pH 5.5. At 2-8° C. and at a protein concentration of 10 mg/ml, a shoulder on the leading edge of the monomer peak was detected by HPSEC. The HPSEC shoulder was not observed after equilibration of MabA for about 80 minutes at 23-27° C. or following dilution to a protein concentration less than or equal to 4 mg/ml. Characterization studies, including analytical ultracentrifugation (AUC), were performed to further understand the nature of the HPSEC shoulder of MabA. The results are summarized below.

The size distribution results obtained by AUC are consistent with the HPSEC data showing that shoulder formation is temperature-dependent. AUC analysis of MabA (10 mg/ml) conducted at 4° C. showed a broadening of the peak at higher S (sedimentation coefficient; Svedbergs), suggesting self-association. No broadening of the peak (self-association) was observed at the same concentration at 25° C.

The self-association is concentration-dependent and decreases with lower antibody concentrations. At 2-8° C. and protein concentrations less than or equal to 4 mg/ml, the shoulder was not observed by HPSEC. Size distribution analyses by AUC at 4° C. also showed less broadening of the product peak at a low protein concentration.

The HPSEC shoulder fraction was collected, re-analyzed by HPSEC, and eluted as a monomer with no shoulder.

At 10 mg/ml (2-8° C.), HPSEC with multi-angle light scattering (MALS) analysis demonstrated that the shoulder has an apparent molecular weight of 213 kDa. This apparent molecular weight is consistent with self-association.

Following a 2 hour equilibration at 23-27° C., MabA (10 mg/ml) was returned to 2-8° C. and the shoulder was not observed by HPSEC within several hours. The result indicates that it takes several hours for the shoulder to be detected at 2-8° C. after room temperature equilibration.

High molecular weight forms are known to cause increased intensity of light scattering compared to monomer. Dissociation of the MabA present in the HPSEC shoulder, (apparent molecular weight of 213 kDa) would, therefore, be expected to result in a decrease in light scattering. A stopped-flow kinetics study with light scattering detection showed that there was a rapid decline in light scattering signal upon dilution of MabA (from 10 mg/mg to 1 mg/ml) at 4° C. Upon the same dilution, control IgG2 and IgG1 antibodies (control antibodies that do not exhibit RSA tendency) showed no decline in light scattering signal. The results suggest that dissociation of the shoulder species following dilution is fast, with an apparent half-life of 14 seconds.

In summary, the shoulder observed by orthogonal size distribution analysis of MabA is shown to be dependent upon temperature and protein concentration, and is not observed following room temperature equilibration of the antibody. The kinetics studies suggest rapid dissociation of MabA present in the shoulder upon dilution and slow re-association at 2-8° C.

It is noted that when evaluating whether RSA has been reduced or eliminated, it is important to perform the HPSEC analysis at a relevant concentration, such as at least 10 mg/ml, e.g., 10 mg/ml or 20 mg/ml. This is important because the measurement of RSA tendency can be falsely skewed by diluting an antibody to a sufficiently low concentration. Thus, an assessment that RSA is not detectable by HPSEC when measured at a concentration of, for example, 1-4 mg/ml, may not be indicative of good RSA characteristics of the antibody when evaluated at a concentration that is closer to the concentration at which the antibody will be stored and/or used. Accordingly, to properly evaluate whether RSA has, in fact, been eliminated and is not measurable by HPSEC at 2-8° C., it is important to conduct the analysis at an appropriate concentration, such as at least about 10 mg/ml, e.g., about 10 mg/ml, about 12 mg/ml, about 15 mg/ml, or about 20 mg/ml. This, however, is not meant to imply that measurements cannot be performed at any of a number of concentrations. Moreover, specifying that RSA is not measurable by HPSEC at 10 mg/ml does not imply that it is measurable at 20 mg/ml. In certain embodiments, RSA is not detectable by HPSEC at 2-8° C. when assessed at a concentration of about 10 mg/ml, about 20 mg/ml and/or at about 50 mg/ml.

Methods of Monitoring Biophysical Characteristics of Antibody

The present disclosure relates, in part, to methods of preventing the RSA tendency of an antibody in a formulation. As such, in some embodiments, a method of evaluating the presence and/or degree of the RSA tendency is useful to determine whether RSA has been prevented upon, e.g., alteration of an antibody formulation. Moreover, such techniques can be used to assay RSA in an initial formulation, such as, to evaluate whether RSA tendency of an antibody in a particular formulation is such that re-formulation is advantageous.

Various analytical techniques and instruments for measuring and comparing certain biophysical characteristics of proteins are available and well-known in the art (see, e.g., Cantor, C. R. and Schimmel, P. R. (1980). *Biophysical Chemistry: Pt. II: Techniques for the Study of Biological Structure and Function*. W. H. Freeman.)

In exemplary embodiments, the presence of RSA can be assessed by the relative size (e.g., average antibody hydrodynamic radius), thermal stability, or changes in secondary/tertiary conformation. In some embodiments, dynamic light scattering (DLS), analytical ultracentrifugation (AUC), or high performance size exclusion chromatography (HPSEC) can be used to determine any changes to the average radius and/or shape of a molecule. Using such methods, the presence or the degree of RSA of antibody in a given formulation can be evaluated and compared.

For example, when RSA of an antibody is evaluated by HPSEC at cold temperature conditions, e.g., 5° C., the antibody molecules typically elute as a monomer species, or dimer species, and the relative amount of each is unique for a given antibody. MabA, for example, elutes primarily as a monomer, with minor presence of dimer. RSA of MabA can be detected by a signature "drag" (or shoulder) at the leading edge of the monomer peak at about 2-8° C. (see FIG. 1A). In contrast, this shoulder is absent in a formulation that prevents MabA RSA at about 2-8° C. (see FIG. 2A). Thus, RSA is significantly reduced and is not measurable by HPSEC when assessed at a relevant concentration, such as 10 mg/ml. In some embodiments, the antibody in a given formulation can be compared, using methods described herein, to a control antibody that does not have RSA tendency.

Further, using DLS at 5° C., antibody size can be measured before and after antibody reformulation and compared to determine whether the reformulation prevented or reduced RSA. For example, the hydrodynamic radius as well as the width of each peak can be compared to determine whether a statistically significant difference exists between two formulations. A statistically significant narrowing of a peak at a given temperature upon reformulation indicates the non-detection of RSA (compare FIGS. 1B and 2B). Alternatively, a statistically significant decrease in hydrodynamic radius of the antibody at 5° C. in a new formulation as compared to a previous formulation indicates that RSA of the antibody has been prevented or reduced as a result of the new formulation.

Additionally, gross conformational changes can be evaluated by monitoring changes to a molecule's secondary or tertiary structure by, e.g., circular dichroism (CD) or second derivative UV, respectively, or by a general assessment of the molecule's thermal stability by, e.g., differential scanning calorimetry (DSC). Other methods to evaluate antibody stability include, for example, charge-transfer absorption, fluorescence spectroscopy, NMR, and HPSEC. See, for example, Wang et al., 1988, J. of Parenteral Science & Technology 42(supp):S4-S26. HPSEC is one of the most common and simplest methods to assess the formation of protein aggregates, protein degradation and protein fragmentation. Accordingly, the stability of the formulations of the present disclosure may be assessed by these methods. Furthermore, an antibody's conformational change as a result of increased hydrophobic surface exposure can be directly measured by 1-anilino-8-naphthalene sulfonate (ANS) binding. ANS is a fluorescent dye known to preferentially bind to hydrophobic patches on protein surfaces. Binding results in an increase in ANS fluorescence intensity, allowing direct assessment of any changes in surface hydrophobicity.

The stability and/or activity of the formulations of the present disclosure also can be assessed by any assays which measure the biological activity of anti-PDGFR-alpha or an antigen-binding fragment thereof in the formulation. The biological activity of an antibody includes, but is not limited to, antigen-binding activity. Antigen-binding activity of anti-PDGFR-alpha or an antigen-binding fragment thereof can be measured by any method known to those skilled in the art, including but not limited to ELISA, radioimmunoassay, Western blot, and the like. An ELISA-based assay, e.g., may be used to compare the ability of a formulation of anti-PDGFR-alpha or an antigen-binding fragment thereof to immunospecifically bind to a PDGFR-alpha antigen to an anti-PDGFR-alpha reference standard.

In evaluating and/or comparing any of the biophysical characteristics of a given antibody, the prevention or reduction of RSA is achieved when a statistically significant difference of a biophysical property can be measured or observed for an antibody in two or more formulations at a given temperature. For example, using HPSEC to evaluate RSA at a relevant concentration, such as 10 mg/ml, the signature MabA monomer peak in formulation A (exhibiting RSA) can be compared to MabA monomer peak in formulation B (the reformulation) at 5° C. If MabA shows an absence of the shoulder in the monomer peak in formulation B, then the prevention or reduction of RSA has been achieved. In other embodiments, the degree of RSA of an antibody in a given formulation can be evaluated by comparing a biophysical property as described herein at two different temperatures (e.g., 5° C. versus 25° C.). For example, upon reformulation of an antibody in a formulation demonstrated to prevent or reduce RSA, the antibody in the new formulation can be evaluated at two different temperatures by, e.g., DLS. If DLS shows that the difference in hydrodynamic radii of the antibody in the formulation at 5° C. and 25° C. are statistically insignificant, then RSA of the antibody has been mitigated as a result of the new formulation. The determination of a statistically significant/insignificant difference is well-known in the art. As noted throughout, when using these methods to evaluate reduction or prevention of RSA, it is important to evaluate at a relevant concentration given the assay. For example, for HPSEC, it is important to evaluate at a relevant concentration, such as 10 mg/ml, because dilution of an antibody in a formulation to a sufficiently low enough concentration can diminish RSA tendency and provide a false assessment of how the antibody performs in the formulation at concentrations that are relevant to storage and/or use conditions. In certain embodiments, the HPSEC evaluation is performed at or near the same concentration as the antibody storage concentration, such as about 20 mg/ml.

It is noted that when evaluating whether RSA has been reduced or eliminated, it is important to perform the HPSEC analysis at a relevant concentration, such as at least 10 mg/ml, e.g., 10 mg/ml, 12 mg/ml, 15 mg/ml, 18 mg/ml, or 20 mg/ml. This is important because the measurement of RSA tendency can be falsely skewed by diluting an antibody to a sufficiently low concentration. Thus, an assessment that RSA is not detectable by HPSEC when measured at a concentration of, for example, 1-4 mg/ml, may not be an accurate indicator of RSA characteristics of the antibody such as when evaluated at a concentration that is closer to the concentration at which the antibody will be stored and/or used. Accordingly, to properly evaluate whether RSA has, in fact, been eliminated and is not measurable by HPSEC at 2-8° C., it is important to conduct the analysis at an appropriate concentration, such as at least 10 mg/ml, e.g, about 10 mg/ml, about 12 mg/ml, about 15 mg/ml, about 18 mg/ml, or about 20 mg/ml. This, however, is not meant to imply that measurements cannot be performed at any of a number of concentrations. Moreover, specifying that RSA is not measurable by HPSEC at 10 mg/ml does not imply that it is measurable at 20 mg/ml. In certain embodiments, RSA is not detectable by HPSEC at 2-8° C. when assessed at a concentration of about 10 mg/ml, about 20 mg/ml and/or at about 50 mg/ml.

The purity of the antibody formulations of the disclosure may be measured by any method well-known to one of skill in the art such as, e.g., HPSEC. The sterility of the antibody formulations may be assessed as follows: sterile soybean-casein digest medium and fluid thioglycollate medium are inoculated with a test antibody formulation by filtering the antibody formulation through a sterile filter having a nominal porosity of 0.45 µm. When using the Sterisure™ or Steritest™ method, each filter device is aseptically filled with approximately 100 ml of sterile soybean-casein digest medium or fluid thioglycollate medium. When using the conventional method, the challenged filter is aseptically transferred to 100 ml of sterile soybean-casein digest medium or fluid thioglycollate medium. The media are incubated at appropriate temperatures and observed three times over a 14 day period for evidence of bacterial or fungal growth.

(iv) Methods of Use (a) Diagnostic Methods of Use

In certain embodiments, reduced RSA formulations of the disclosure may be used in vivo and/or in vitro. By way of example, formulations of the disclosure comprising an anti-PDGFR-alpha antibody or antibody fragment that specifically binds to PDGFR-alpha (e.g., an antibody or fragment comprising one or more CDRs set forth in Table 1; an antibody or fragment comprising all six CDRs set forth in Table 1; an antibody or fragment that binds to the same epitope as an antibody or fragment comprising all six CDRs set forth in Table 1; an antibody or fragment comprising one or both of the VH and VL domains set forth in Table 1; an antibody or fragment that binds to the same epitope as an antibody or fragment comprising one or both of the VH and VL domains set forth in Table 1; etc.) can be used in vivo and/or in vitro, such as for detecting PDGFR-alpha expression in cells and tissue or for imaging PDGFR-alpha expressing cells and tissues. In certain embodiments, the antibodies are human antibodies and such antibodies are used to image PDGFR-alpha expression in a living human patient.

By way of example, diagnostic uses can be achieved, for example, by contacting a sample to be tested, optionally along with a control sample, with the antibody under conditions that allow for formation of a complex between the antibody and PDGFR-alpha. Complex formation is then detected (e.g., using an ELISA or by imaging to detect a moiety attached to the antibody). When using a control sample along with the test sample, complex is detected in both samples and any statistically significant difference in the formation of complexes between the samples is indicative of the presence of PDGFR-alpha in the test sample.

In one embodiment, the disclosure provides a method of determining the presence of PDGFR-alpha in a sample suspected of containing PDGFR-alpha, said method comprising exposing the sample to an anti-PDGFR-alpha antibody in a formulation of the disclosure, and determining binding of the antibody to PDGFR-alpha in the sample wherein binding of the antibody to PDGFR-alpha in the sample is indicative of the presence of the PDGFR-alpha in the sample. In one embodiment, the sample is a biological sample. In an exemplary embodiment, the method is used in vitro to evaluate whether a cancerous or potentially cancerous sample, such as a tumor biopsy, contains cells that express or over express PDGFR-alpha. Such an in vitro diagnostic could be used to evaluate whether the patient is particularly likely to respond to treatment with an anti-PDGFR-alpha antibody.

In certain embodiments, the anti-PDGFR-alpha antibodies in the formulations of the disclosure may be used to detect the overexpression or amplification of PDGFR-alpha using an in vivo diagnostic assay. In one embodiment, the anti-PDGFR-alpha antibody is added to a sample wherein the antibody binds the PDGFR-alpha to be detected and is tagged with a detectable label (e.g. a radioactive isotope or a fluorescent label) and externally scanning the patient for localization of the label.

Alternatively, or additionally, FISH assays such as the INFORM™ (sold by Ventana, Ariz.) or PATHVISION™ (Vysis, Ill.) may be carried out on formalin-fixed, paraffin-embedded tissue to determine the extent (if any) of PDGFR-alpha expression or overexpression in a sample.

In certain embodiments of any of the foregoing, the diagnostic assay is performed on a human patient or a sample from a human patient, and the anti-PDGFR-alpha antibody specifically binds to human PDGFR-alpha. Note that, optionally, the anti-PDGFR-alpha antibody also specifically binds to PDGFR-alpha from one or more other species, thereby facilitating the use and/or testing of the antibody in both humans and in suitable animal models.

Note that other exemplary anti-PDGFR-alpha antibodies that specifically bind to PDGFR-alpha, and that can be formulated as provided herein, are provided in U.S. application publication 2008-0089837, which is incorporated by reference in its entirety. The disclosure contemplates that any such antibodies may be formulated as described herein and used, for example, in a diagnostic method.

(b) Therapeutic Methods of Uses

In certain embodiments, the disclosure contemplates that antibodies and formulations described herein may be used therapeutically, for example, in the treatment of human or non-human subjects. In certain embodiments, the formulations are non-RSA detected formulations of the disclosure. By way of example, formulations, as described herein, comprising an anti-PDGFR-alpha antibody or antibody fragment that specifically binds to PDGFR-alpha (e.g., an antibody or fragment comprising one or more CDRs set forth in Table 1; an antibody or fragment comprising all six CDRs set forth in Table 1; an antibody or fragment that binds to the same epitope as an antibody or fragment comprising all six CDRs set forth in Table 1; an antibody or fragment comprising one or both of the VH and VL domains set forth in Table 1; an antibody or fragment that binds to the same epitope as an antibody or fragment comprising one or both of the VH and VL domains set forth in Table 1; etc.) may be administered as part of a method of treating a human or non-human subject. In certain embodiments, the formulation for use in a therapeutic method is a formulation for which RSA of the antibody or fragment is prevented or reduced relative to an initial formulation. In other embodiments, the formulation is a formulation for which RSA of the antibody or antibody fragment is not measurable by HPSEC at about 2-8° C., when assessed at a concentration of at least about 10 mg/ml.

In certain aspects, the formulations comprising an anti-PDGFR-alpha antibody or antibody fragment, according to the disclosure, may be administered for treatment of a subject in need thereof, such as a human subject. Exemplary conditions that can be treated include, but are not limited to neoplastic conditions. Further exemplary conditions are those associated with overexpression or misregulation of PDGFR-alpha or PDGFR-alpha signaling.

In certain aspects, the disclosure provides a method of treating a neoplastic condition in a subject in need thereof, comprising administering to said subject a therapeutically effective amount of a formulation as described herein comprising an anti-PDGFR-alpha antibody that specifically binds to PDGFR-alpha. Suitable antibodies for use in such formulations are described herein, as well as in US Patent Publication 2008-0089837, which is incorporated by reference in its entirety. Any of the diseases detailed herein, such as any of the neoplastic diseases described herein, can be treated. Further, the disclosure contemplates that any such formulations can be used as part of a therapeutic regimen appropriate for the particular condition. By way of example, suitable regimens may include, in addition to an anti-PDGFR-alpha antibody formulated as described herein, one or more of (i) one or more other agents, such as chemotherapeutic agents, other antibodies, other small molecule inhibitors; (ii) radiotherapy; (iii) surgery; (iv) a dietary regimen; (v) bone marrow transplant; (vi) stem cell transplant; (vii) dialysis; (viii) physical therapy; (ix) skin grafting; (x) acupuncture; (xi) oxygen therapy; (xii) insulin therapy; (xiii) smoking cessation; and the like. Therapeutic interventions that are not drugs or biological agents are also referred to herein as other therapeutic modalities or other therapies. Exemplary agents and combinations of agents are described below.

Particularly suitable antibodies (and fragments) for use in the treatment of cancers specifically bind to PDGFR-alpha and inhibit the growth of cells that express PDGFR-alpha, as well as formulations thereof. Examples include antibodies comprising the sequences set forth in Table 1 and/or antibodies that bind to the same epitope and/or antibodies provided in application Ser. No. 11/833,473. Suitable antibodies can similarly be described based on their affinity for PDGFR-alpha, based on their ability to block the binding of ligand to PDGFR-alpha, and based on neutralization ability. Suitable methods for characterizing the activity of a PDGFR-alpha antibody are known in the art and are also set forth in U.S. Patent Publication 2008-0089837, which is incorporated by reference in its entirety.

Regardless of the particular formulation administered, an effective amount is administered to patients. As used herein, the term "effective amount" refers to the amount of a therapy which is sufficient to reduce and/or ameliorate the severity and/or duration of a disease or disorder; prevent or delay the advancement of said disease or disorder; cause regression of said disease or disorder; prevent or delay the recurrence, development, or onset of one or more symptoms associated with said disease or disorder, or enhance or improve the effect(s) of another therapy. It is understood that measurable signs of effectiveness may not be observable following a single dose.

"Treating" a condition or disease refers to curing as well as ameliorating at least one symptom of the condition or disease, and includes administration of a composition which reduces the frequency of, or delays the onset of, symptoms of a medical condition in a subject in need relative to a subject which does not receive the composition. Thus, treating cancer includes, for example, reducing the number of detectable cancerous growths in a population of patients receiving a treatment relative to an untreated control population, and/or delaying the appearance of detectable cancerous growths in a treated population versus an untreated control population, e.g., by a statistically and/or clinically significant amount. By way of further example, treating cancer includes, for example, delaying disease progression, delaying or preventing metastases, reducing the number of metastases, increase life span, reducing pain (e.g., such as by reducing the size of tumor(s) that are causing pain). As another example, treatment of pain includes reducing the magnitude of, or alternatively delaying, pain sensations experienced by subjects in a treated population versus an untreated control population.

In certain embodiments, progress and effectiveness of treatment is monitored during and/or following treatment. For example, neoplastic conditions can be monitored using methods suitable for the particular condition, such as blood tests, fecal analysis, X-ray, CT scan, MRI, biopsy, PET scan, and the like. Moreover, treatment may be monitored based on assessment of improvement in symptoms, such as decreased pain (e.g., patient requests/uses less pain medication), decreased reliance on supplemental oxygen, improvement in appetite, weight gain, decreased fatigue, increased mobility, and the like.

The present disclosure provides, in part, antibody-based therapies which involve administering to a subject, preferably a human, the antibody formulations (or "antibody formulations" or "formulations") described herein for treating, managing or ameliorating a disease or disorder associated with or characterized by aberrant expression and/or activity of PDGFR-alpha. For example, the antibodies can inhibit growth of cells expressing PDGFR-alpha, thereby inhibiting tumor growth, or the antibodies can be associated with an agent and deliver a lethal toxin to a targeted cell. In a particular embodiment, the formulations of the disclosure are used to treat a neoplastic disease, such as any one or more of the diseases detailed below. Anti-PDGFR-alpha antibodies can have therapeutic effects in treating fibrotic diseases, such as cardiac, lung, liver, kidney or skin fibrosis. Anti-PDGFR-alpha antibodies can also have therapeutic effects in the treatment of allograft vasculopathy or restenosis. In addition, the anti-PDGFR-alpha antibodies are useful as diagnostics for the disease states, especially neoplastic, fibrotic and immune system diseases.

Exemplary treatable neoplastic diseases, include, for example, cancers including, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies, epidermoid carcinoma, and gastrointestinal stromal tumor (GIST). In certain embodiments, the method comprises treating any one or more of the foregoing cancers, wherein the cancer is the primary site of disease (e.g., primary tumor). In certain other embodiments, the method comprises treating any one or more of the foregoing cancers, wherein the cancer is metastatic.

In certain embodiments, the method comprises treating glioblastoma, wherein the glioblastoma is glioblastoma multiforme. In certain embodiments, the method comprises treating ovarian cancer. In certain embodiments, the method comprises treating hepatocellular carcinoma. In certain embodiments, the method comprises treating non-small cell lung cancer. In certain embodiments, the method comprises treating kidney cancer, wherein the kidney cancer is renal cell carcinoma (RCC), metastatic RCC, or clear cell RCC. The disclosure contemplates treating such diseases as primary tumors and/or metastatic disease.

In certain embodiments, the method comprises treating any one or more of the following cancers: desmoplastic small round cell tumor, glioblastoma multiforme, desmoid tumor, chondrosarcoma, advanced neuroendocrine tumors, renal cell carcinoma (including metastatic RCC), clear cell RCC, dermatofibrosarcoma, metastatic melanoma, Merkel cell carcinoma, giant cell fibroblastoma (GCF), HIV-related Kaposi's sarcoma, cervical cancer, testicular cancer, anal cancer, gall bladder cancer, and bone cancer. The disclosure contemplates treating such diseases as primary tumors and/or metastatic disease.

In certain embodiments, the method comprises treating a hematopoietic or hematological malignancy, such as hypereosinophilic syndrome (HES); polycythemia vera (PV); myeloma (including multiple myeloma); leukemia; or lymphoma. In certain embodiments, the malignancy is a leukemia or lymphoma, such as acute myelogenous leukemia (AML); acute lymphocytic leukemia (ALL); chronic myelogenous leukemia (CML); chronic lymphocytic leukemia (CLL); hairy cell leukemia; Hodgkin lymphoma; or non-Hodgkin lymphoma (e.g., mantle cell lymphoma, lymphoblastic lymphoma, Burkitt lymphoma, follicular lymphoma, cutaneous T-cell lymphoma, etc.).

The disclosure provides methods comprising administration of formulations comprising anti-PDGFR-alpha antibodies that specifically bind to PDGFR-alpha, such as the formulations and antibodies described herein. Such methods include methods of treating any of the foregoing cancers by administering an effective amount of said antibody formulated, as described herein. Moreover, the methods include administering such formulations as part of a therapeutic regimen in combination with one or more other agents and/or one or more other treatment modalities. Note, however, that methods wherein administration of PDGFR-alpha antibodies (or fragments) are the sole therapy (e.g., monotherapy) are also contemplated.

As noted above, the disclosure provides that, in certain embodiments, the formulations comprising anti-PDGFR-alpha antibodies are administered as part of a therapeutic regimen with one or more other agents and/or one or more other treatment modalities. Any of these other agents and/or treatment modalities may be used in combination with an anti-PDGFR-alpha antibody to treat any of the foregoing cancers or conditions. The selection of suitable other agents and/or treatment modalities may depend on the particular disease, condition of the patient, age of the patient, symptoms, and the like. By way of example, other suitable treatment modalities include, but are not limited to, surgery, radiotherapy, bone marrow transplant, stem cell transplant, dialysis, insulin therapy, diet, physical therapy, smoking cessation, oxygen therapy, ventilatory support, acupuncture, and the like. By way of example, other suitable agents include, but are not limited to chemotherapeutic agents, hormones, narcotics (such as, for pain management), anti-inflammatories, antibiotics, anti-virals, anti-fungals, analgesics, and the like. Any one or more of these agents and/or modalities can be used as part of a therapeutic regimen.

Any suitable agents, such as those which are known to be useful, or which has been used or is currently being used for the prevention, management, treatment, or amelioration of one or more symptoms associated with a disease or disorder associated with or characterized by aberrant expression and/or activity of a PDGFR-alpha polypeptide, an autoimmune disease, an inflammatory disease, a proliferative disease, or an infection, can be used in combination with the antibody formulations of the present disclosure as part of a therapeutic method for the treatment of any one or more of the conditions, such as any one or more of the cancers detailed herein.

In certain embodiments, a suitable therapeutic regimen includes one or more agents, in addition to an anti-PDGFR-alpha antibody (e.g., such as an anti-PDGFR-alpha antibody or antibody fragment formulated as provided herein), possessing a pharmaceutical property selected from anti-mitotic, alkylating, anti-metabolite, anti-angiogenic, apoptotic, alkaloid, COX-2, and antibiotic agents and combinations thereof. By way of example, in certain embodiments, the drug can be selected from the group of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, anti-metabolites, antibiotics, enzymes, epipodophyllotoxins, platinum coordination complexes, vinca alkaloids, substituted ureas, methyl hydrazine derivatives, adrenocortical suppressants, endostatin, taxols, camptothecins, oxaliplatin, doxorubicins and their analogs, and a combination thereof.

Further non-limiting examples of agents of use as part of a therapeutic regimen for treating cancerous conditions, such as any of the cancerous conditions described herein, include anthracyclines, such as doxorubicin (adriamycin), daunorubicin (daunomycin), idarubicin, detorubicin, caminomycin, epirubicin, esorubicin, and morpholino and substituted derivatives, combinations and modifications thereof. Further examples of agents of use as part of a therapeutic regimen for treating cancerous conditions, such as any of the cancerous conditions described herein, include cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide, and bleomycin, and derivatives, combinations and modifications thereof. In certain embodiments, the agent is doxorubicin, morpholinodoxorubicin, or morpholinodaunorubicin. As noted herein, therapeutic regimens may include any one or more additional agents and/or any one or more additional therapeutic modalities. Although, in certain embodiments, the anti-PDGFR-alpha antibody is administered as a monotherapy, and the regimen does not include further therapies.

To illustrate briefly, below is provided a list of other agents that can be used, alone or in combination with each other and/or with other therapies, as part of a combination method. Suitable agents include:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); anti-metabolites (for example gemcitabine and antifolates such as fluoropyrimidines like 5-fluorouracil and tegafur, raltitrexed, methotrexate, cytosine arabinoside, and hydroxyurea); anti-tumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5-α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethox-y]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-met-hylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or, inhibitors of cathepsins, inhibitors of serine proteases for example matriptase, hepsin, urokinase, inhibitors of heparanase;

(iv) cytotoxic agents such as fludarabine, 2-chlorodeoxyadenosine, chlorambucil or doxorubicin and combination thereof such as Fludarabine+cyclophosphamide, CVP: cyclophosphamide+vincristine+prednisone, ACVBP: doxorubicin+cyclophosphamide+vindesine+bleomycin+prednisone, CHOP: cyclophosphamide+doxorubicin+vincristine+prednisone, CNOP: cyclophosphamide+mitoxantrone+vincristine+prednisone, m-BACOD: methotrexate+bleomycin+doxorubicin+cyclophosphamide+vincristine+dexamethasone+leucovorin, MACOP-B: methotrexate+doxorubicin+cyclophosphamide+vincristine+prednisone fixed dose+bleomycin+leucovorin, or ProMACE CytaBOM: prednisone+doxorubicin+cyclophosphamide+etoposide+cytarabine+bleomycin+vincristine+methotrexate+leucovorin;

(v) inhibitors of growth factor function, for example such inhibitors include growth factor antibodies and growth factor receptor antibodies (for example the anti-erbB2 antibody trastuzumab [Herceptin®], the anti-EGFR antibody panitumumab, the anti-erbB1 antibody cetuximab [Erbitux] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazol-in-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors, aurora kinase inhibitors (for example AZD1152, PH739358, VX-680, MLN8054, R763, MP235, MP529, VX-528 and AX39459), cyclin dependent kinase inhibitors such as CDK2 and/or CDK4 inhibitors, and inhibitors of survival signaling proteins such as Bcl-2, Bcl-XL for example ABT-737;

(vi) antiangiogenic agents such as those which inhibit the effects of vascular endothelial growth factor, [for example the anti-vascular endothelial cell growth factor antibody bevacizumab (Avastin®) and VEGF receptor tyrosine kinase inhibitors such as 4-(4-bromo-2-fluoroanilino)-6-methoxy-7-(1-methylpiperidin-4-ylmethoxy)qu-inazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856, WO 98/13354, WO00/47212 and WO01/32651 and compounds that work by other mechanisms (for example linomide, inhibitors of integrin .alpha.v.beta.3 function and angiostatin)] or colony stimulating factor 1 (CSF1) or CSF1 receptor;

(vii) vascular damaging agents such as Combretastatin A4 and compounds disclosed in International Patent Applications WO 99/02166, WO 00/40529, WO 00/41669, WO 01/92224, WO 02/04434 and WO 02/08213;

(viii) antisense therapies, for example those which are directed to the targets listed above, such as G-3139 (Genasense), an anti bcl2 antisense;

(ix) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (x) immunotherapy approaches, including for example treatment with Alemtuzumab (campath-1H®), a monoclonal antibody directed at CD52, or treatment with antibodies directed at CD22, ex vivo and in vivo approaches to increase the immunogenicity of patient tumour cells, transfection with cytokines such as interleukin 2, interleukin 4 or granulocyte macrophage colony stimulating factor, approaches to decrease T cell anergy such as treatment with monoclonal antibodies inhibiting CTLA-4 function, approaches using transfected immune cells such as cytokine transfected dendritic cells, approaches using cytokine transfected tumour cell lines and approaches using anti idiotypic antibodies;

(xi) inhibitors of protein degradation such as proteasome inhibitor such as Velcade (bortezomid).

In an exemplary embodiment, antibody formulations of the present disclosure (formulations comprising an anti-PDGFR-alpha antibody) may be administered in combination with temozolomide as part of a method for treating glioblastoma mutiforme. In another exemplary embodiment, antibody formulations of the present disclosure (formulations comprising an anti-PDGFR-alpha antibody) may be administered in combination with topotecan as part of a method for treating ovarian cancer. In another exemplary embodiment, antibody formulations of the present disclosure (formulations comprising an anti-PDGFR-alpha antibody) may be administered in combination with Sorafenib as part of a method for treating hepatocellular carcinoma. In another exemplary embodiment, antibody formulations of the present disclosure (formulations comprising an anti-PDGFR-alpha antibody) may be administered in combination with one or more of cediranib, docetaxel, and carboplatin as part of a method for treating non-small cell lung carcinoma. In another exemplary embodiment, antibody formulations of the present disclosure (formulations comprising an anti-PDGFR-alpha antibody) may be administered in combination with both carboplatin and paclitaxel, or in combination with both gemcitabine and cisplatin as part of a method for treating non-small cell lung carcinoma. The foregoing specific examples are merely illustrative. The disclosure contemplates, in certain embodiments, methods of administering formulations of the description as part of a therapeutic regimen along with any one or more of the foregoing agents and/or one or more other treatment modalities. Any such combination therapy may be used in a method of treating, for example, any of the cancerous diseases described herein.

For any methods of treating involving administering a combination of agents and/or therapies, such conjoint treatment may be achieved by way of the simultaneous, sequential or separate dosing of the individual components of the treatment. For any of the foregoing methods, including combination therapies or monotherapy, the disclosure contemplates that, in certain embodiments, the antibody is MabA. In certain embodiments, the antibody is MabA formulated as provided herein.

(v) Dosage and Administration

Embodiments of the disclosure include sterile pharmaceutical formulations of anti-PDGFR-alpha antibodies that are useful as treatments for diseases. Such formulations would inhibit cell growth, thereby effectively treating pathological conditions where, for example, PDGFR-alpha expression is abnormally elevated or PDGFR-alpha expressing cells mediate disease states. Anti-PDGFR-alpha antibodies preferably possess adequate affinity to specifically bind PDGFR-alpha, and preferably have an adequate duration of action to allow for dosing in humans. A prolonged duration of action will allow for less frequent and more convenient dosing schedules.

Various delivery systems are known and can be used to administer a formulation of the present description. Methods of administering antibody formulations of the present disclosure or a therapy include, but are not limited to, parenteral administration (e.g., intradermal, intramuscular, intraperitoneal, intravenous and subcutaneous), epidural administration, topical administration, and mucosal administration (e.g., intranasal and oral routes). In a specific embodiment, formulations of the present disclosure are administered intramuscularly, intravenously, or subcutaneously. In a preferred embodiment, the formulations of the disclosure are administered intravenously, such as by intravenous infusion. The formulations may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a specific embodiment, the formulations of the disclosure are administered intratumorally or at the site of inflammation. Note that when the formulations are administered as part of a combination therapy, the disclosure contemplates that other agents may be administered by the same or different route of administration.

In a specific embodiment, the antibody formulations of the disclosure comprise a pharmaceutically acceptable carrier. In a preferred embodiment, the pharmaceutically acceptable carrier is water for injection, USP, 5% dextrose in water (D5W) or saline.

In certain embodiments, the formulations comprise antibody at a concentration of about 1 mg/ml, 5 mg/ml, 10 mg/ml, 15 mg/ml, 20 mg/ml, 25 mg/ml, 30 mg/ml, 40 mg/ml, 50 mg/ml, 60 mg/ml, 70 mg/ml, 75 mg/ml, 80 mg/ml, 90 mg/ml, or at about 100 mg/ml. In certain embodiments, the formulations comprise an antibody at a concentration of about 20 mg/ml or of about 50 mg/ml.

The precise dose to be employed and the dosing regimen will depend on the route of administration, the specific disease to be treated, the severity of the patient's condition, and the like. Effective doses may be extrapolated from dose-response curves derived from in vitro or animal model test systems.

For formulations of the antibodies, the dosage administered to a patient may be calculated using the patient's weight in kilograms (kg) multiplied by the dose to be administered in mg/kg. The required volume (in mL; also referred to interchangeably as ml) to be given is then determined by taking the mg dose required divided by the concentration of the antibody formulation. If needed, the final calculated required volume may be obtained by pooling the contents of as many vials as are necessary into syringe(s) to administer the antibody formulation of the disclosure. The final calculated required volume will be obtained by pooling the contents of as many vials as are necessary into syringe(s) or bags to administer the drug. In certain embodiments, a maximum volume of 2.0 mL of the antibody formulation is injected per site. The dose (in mL; also referred to interchangeably as ml) can be calculated using the following formula: Dose (mL)=[volunteer weight] (kg)×[dose]mg/kg/20 mg/mL of the antibody formulation. Generally, human antibodies have a longer half-life within the human body than antibodies from other species due to the immune response to the foreign polypeptides. Thus, lower dosages of human antibodies and less frequent administration is often possible. Further, the dosage, volume and frequency of administration of formulations of the present disclosure may be reduced by increasing the concentration of an antibody (including antibody fragment thereof) in the formulations, increasing affinity and/or avidity of the antibody (including antibody fragment thereof), and/or increasing the half-life of the antibody (including antibody fragment thereof).

In a specific embodiment, the dosage administered to a patient will be calculated using the patient's weight in kilograms (kg) multiplied by the dose to be administered in mg/kg. The required volume (in mL) to be given is then determined by taking the mg dose required divided by the concentration of the antibody (including antibody fragment thereof) in the formulations (such as 20 mg/mL, 50 mg/mL, or 100 mg/mL).

In certain embodiments, particularly in the case of formulations intended for administration to humans, the formulations are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less than 10 EU/mg, or less then 5 EU/mg, or less than 1 EU/mg, or less than 0.1 EU/mg, or less than 0.01 EU/mg, or less than 0.001 EU/mg.

As discussed herein, when RSA tendency of an antibody in a particular formulation is significant, safe and effective use of the formulation may require long incubation periods at room temperature to help eliminate or reduce RSA that occurs at storage temperatures. Such required incubation periods introduce variation among patients and users, create potential compliance problems, undermine the potential for administration at home, and introduce significant time delays and administrative burdens into a treatment scheme. One benefit of formulations with eliminated or reduced RSA tendency, particularly formulations in which the eliminated or reduced RSA tendency of the antibody does not significantly vary with temperature and/or concentration, is the elimination or reduction of the requirement to incubate the formulations at room temperature for long periods of time (e.g., greater than or equal to about 60-90 minutes). Accordingly, in certain embodiments, the administered formulations and/or instructions for doing so do not specify or require the need to equilibrate the formulation to room temperature, e.g., to incubate the formulation at room temperature for at least 60 minutes following cold storage (less than about 8° C.) and prior to administration. In certain other embodiments, the instructions provided explicitly indicate that the formulation can be administered, following cold storage, without a need or requirement to incubate the formulation at room temperature for at least 60 minutes.

In certain embodiments, the formulations of the present disclosure exhibit stability at the temperature range of 38-42° C. for at least 15 days and, in some embodiments, not more than 1 month. Additionally or alternatively, in certain embodiments, the formulations are stable at the temperature range of 20° C.-24° C. or 23° C.-27° C. for at least 6 months and/or at the temperature range of 2° C.-8° C. for at least 6 months, at least 1 year, at least 1.5 years, at least 2 years, at least 2.5 years, at least 3 years or at least 4 years. Additionally or alternatively, in certain embodiments, the formulations are stable at the temperature of −20° C. for at least 2 years, at least 3 years, at least 4 years, or at least 5 years. Stability may be as assessed, for example, by high performance size exclusion chromatography (HPSEC). In certain embodiments, stability can be assessed by maintenance of a level of purity over time. For example, in certain embodiments, formulations of the present description have less than 1%, less than 0.8%, less than 0.75%, less than 0.7%, less than 0.6%, less than 0.5%, or even less than 0.4% loss of purity/year when stored at 2-8° C., as determined by HPSEC. In one embodiment, formulations of the present disclosure have a shelf-life of greater than 6 months, greater than 1 year, or greater than 18 months with less than 0.2% purity loss over 6 months at 2-8° C. as determined by HPSEC, which monitors the presence or absence of fragments and/or high molecular weight forms.

(vi) Articles of Manufacture

The disclosure provides a pharmaceutical pack or kit comprising one or more containers filled with a formulation of the description. Similarly, the disclosure provides a pharmaceutical pack or kit suitable for laboratory and/or diagnostic use. The disclosure contemplates that any of the formulations described herein, such as formulations comprising anti-PDGFR-alpha antibodies having eliminated or reduced RSA tendency, can be packaged and sold as part of a kit. Exemplary such kits are pharmaceutical kits.

In a specific embodiment, the formulations of the disclosure comprise antibodies (including antibody fragments thereof) recombinantly fused or chemically conjugated to another moiety, including but not limited to, a heterologous protein, a heterologous polypeptide, a heterologous peptide, a large molecule, a small molecule, a marker sequence, a diagnostic or detectable agent, a therapeutic moiety, a drug moiety, a radioactive metal ion, a second antibody, and a solid support. The disclosure also provides a pharmaceutical pack or kit comprising in one or more first containers a formulation as described herein and in one or more second containers one or more other prophylactic or therapeutic agents useful for the prevention, management or treatment of a disease or disorder associated with or characterized by aberrant expression and/or activity of PDGFR-alpha.

In an exemplary embodiment, the formulations of the disclosure are formulated in single dose vials as a sterile formulation containing 50 mM sodium-acetate, 10% (w/v) sucrose, and 0.05% (w/v) PS80. Each 1.0 mL of solution contains, in certain embodiments, 20 mg or 50 mg of an anti-PDGFR-alpha antibody (including antibody fragment thereof). During the manufacturing process, the pH of the formulation buffer is adjusted to 5.5.

Any of the formulations of the disclosure may be supplied in 20 mm, 10R Schott type I borosilicate clear glass vials, USP/EP (West Pharmaceutical Serices) with a target volume of, e.g., 10.5 mL. The vials are aseptically stoppered with 20 mm West 4432/50 chlorobutyl Teflon-faced stoppers. The vials are sealed with West aluminum (TruEdge) Flip-Off overseals. Optionally associated with such container(s) can be a notice in the form prescribed by a governmental agency regulating the manufacture, use or sale of pharmaceuticals or biological products, which notice reflects approval by the agency of manufacture, use or sale for human administration.

In the case of kits sold for laboratory and/or diagnostic use, the kit may optionally contain a notice indicating appropriate use, safety considerations, and any limitations on use. Moreover, in the case of kits sold for laboratory and/or diagnostic use, the kit may optionally comprise one or more other reagents, such as positive or negative control reagents, useful for the particular diagnostic or laboratory use.

The present disclosure provides kits that can be used in the above methods. In one embodiment, a kit comprises a formulation as described herein, in one or more containers. In another embodiment, a kit comprises a formulation as described herein, in one or more containers, and one or more other prophylactic or therapeutic agents useful for the prevention, management or treatment of a disease or disorder associated with or characterized by aberrant expression and/or activity of PDGFR-alpha, in one or more other containers. In a specific embodiment, the antibodies (including antibody fragments thereof) included in said formulations comprise one or more of the VH CDRs and/or one or more of the VL CDRs listed in Table 1, supra. Preferably, the kit further comprises instructions for preventing, treating, managing or ameliorating a disorder (e.g., using the formulations of the description alone or in combination with another prophylactic or therapeutic agent), as well as side effects and dosage information for method of administration.

The present disclosure also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient, e.g., an above-described antibody that immunospecifically binds to PDGFR-alpha, is sterile and suitable for administration as a particulate free solution. In certain embodiments, the formulation is suitable for intravenous administration, such as for intravenous infusion.

In a preferred embodiment, the unit dosage form is suitable for intravenous, intramuscular, intranasal, oral, topical or subcutaneous delivery. Thus, the disclosure encompasses solutions, preferably sterile, suitable for each delivery route.

As with any pharmaceutical product, the packaging material and container are designed to protect the stability of the product during storage and shipment. Further, the products of the disclosure include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, etc., and other monitoring information.

Specifically, the disclosure provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a formulation containing an antibody that immunospecifically binds to PDGFR-alpha and wherein said packaging material includes instruction means which indicate that said antibody can be used to prevent, manage, treat, and/or ameliorate one or more symptoms associated with a disorder associated with aberrant expression and/or activity of PDGFR-alpha by administering specific doses and using specific dosing regimens as described herein.

The disclosure also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing an antibody that immunospecifically binds to PDGFR-alpha and the other pharmaceutical agent comprises a prophylactic or therapeutic agent other than an antibody that immunospecifically binds to PDGFR-alpha, and wherein said packaging material includes instruction means which indicate that said agents can be used to treat, prevent and/or ameliorate one or more symptoms associated with a disorder associated with aberrant expression and/or activity of PDGFR-alpha, or one or more symptoms thereof by administering specific doses and using specific dosing regimens as described herein.

In certain embodiments, particularly in the case of pharmaceutical kits comprising formulations intended for administration to humans, the formulations are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

In certain embodiments, the kit comprises a formulation in which the antibody or antibody fragment RSA tendency is eliminated or reduced, such as RSA that is not measurable by HPSEC at 2-8° C. when assessed at a concentration of 10 mg/mL. As discussed herein, when RSA tendency of an antibody in a particular formulation is significant, safe and effective use of the formulation may require long incubation periods at room temperature to help eliminate RSA that occurs at storage temperatures. Such required incubation periods introduce variation among patients and users, create potential compliance problems, undermine the potential for administration at home, and introduce significant time delays and administrative burdens into a treatment scheme. One benefit of formulations with reduced or eliminated RSA tendency, particularly formulations in which the reduced or eliminated RSA tendency of the antibody does not significantly vary with temperature, is the elimination of the requirement to incubate the formulations at room temperature for long periods of time (e.g., greater than or equal to about 60-90 minutes). Accordingly, in certain embodiments, the instructions provided with any of the foregoing kits do not specify or require the need to incubate the formulation at room temperature for at least 60 minutes following cold storage (at about 2 to 8° C.) and prior to administration. In certain other embodiments, the instructions provided with any of the foregoing kits explicitly indicate that the formulation can be administered, following cold storage, without a need or requirement to incubate the formulation at room temperature for at least 60 minutes.

EXAMPLES

The examples below are given so as to illustrate the practice of this invention. They are not intended to limit or define the entire scope of this invention.

Example 1

Initial Characterization of the RSA Tendency of MabA in an Initial Formulation—RSA of MabA is Dependent on Temperature and/or Concentration RSA tendency of MabA in an initial, non-sucrose containing formulation was evaluated at an antibody concentration of 10 mg/ml. In addition to antibody, the initial formulation contained, in water, 50 mM sodium-acetate, 100 mM NaCl, 0.01% (w/v) PS80, pH 5.5. At 2-8° C. and at a protein concentration of 10 mg/ml, a shoulder on the leading edge of the monomer peak was detected by HPSEC. The HPSEC shoulder was not observed after equilibration of MabA for about 80 minutes at 23-27° C. or following dilution to a protein concentration of about 4 mg/ml. Characterization studies, including analytical ultracentrifugation (AUC), were performed to further understand the nature of the HPSEC shoulder of MabA. The results are summarized below.

The size distribution results obtained by AUC are consistent with the HPSEC data showing that shoulder formation is temperature-dependent. AUC analysis of MabA (10 mg/ml) conducted at 4° C. showed a broadening of the peak at higher S (sedimentation coefficient; Svedbergs), suggesting self-association. No broadening of the peak (self-association) was observed at the same concentration at 25° C.

The self-association is concentration-dependent and decreases with lower antibody concentrations. At 2-8° C. and protein concentrations less than or equal to 4 mg/ml, the shoulder was not observed by HPSEC. Size distribution analyses by AUC at 4° C. also showed less broadening of the product peak at a low protein concentration.

The HPSEC shoulder fraction was collected, re-analyzed by HPSEC, and eluted as a monomer with no shoulder.

At 10 mg/ml (2-8° C.), HPSEC with multi-angle light scattering (MALS) analysis demonstrated that the shoulder has an apparent molecular weight of 213 kDa. This apparent molecular weight is consistent with self-association.

Following a 2 hour equilibration at 23-27° C., MabA (10 mg/ml) was returned to 2-8° C. and the shoulder was not observed by HPSEC within several hours. The result indicates that it takes several hours for the shoulder to be detected at 2-8° C. after room temperature equilibration.

High molecular weight forms are known to cause increased intensity of light scattering compared to monomer. Dissociation of the MabA present in the HPSEC shoulder, (apparent molecular weight of 213 kDa) would, therefore, be expected to result in a decrease in light scattering. A stopped-flow kinetics study with light scattering detection showed that there was a rapid decline in light scattering signal upon dilution of MabA (from 10 mg/mg to 1 mg/ml) at 4° C. Upon the same dilution, control IgG2 and IgG1 antibodies (control antibodies that do not exhibit RSA tendency) showed no decline in light scattering signal. The results suggest that dissociation of the shoulder species following dilution is fast, with an apparent half-life of 14 seconds.

In summary, the shoulder observed by orthogonal size distribution analysis of MabA is shown to be dependent upon temperature and protein concentration, and is not observed following room temperature equilibration of the antibody. The kinetics studies suggest rapid dissociation of MabA present in the shoulder upon dilution and slow re-association at 2-8° C.

Example 2

Elimination of MabA RSA Tendency in Sucrose-Containing Formulation as Determined by HPSEC, AUC and DLS MabA Exhibits RSA Tendency in Various Formulations Including the Acetate/Salt Formulation Under Cold Temperature Storage Conditions The RSA tendency of MabA in an initial, non-sucrose-containing, acetate/salt formulation (10 mg/ml MabA, 50 mM Na-acetate, 100 mM NaCl, 0.01% (w/v) PS80, pH 5.5) was evaluated by high performance size exclusion chromatography (HPSEC) at standard storage temperature (at about 2-8° C.) and at room temperature (at about 23-27° C.). As shown in FIG. 1A, RSA tendency of MabA is pronounced at about 2-8° C., as indicated by a leading edge shoulder on the monomer peak. Such a leading edge shoulder was not detected when tested at 25° C., indicating that MabA behaves differently at 2-8° C. as compared at 23-27° C. More specifically, MabA exhibits significant RSA tendency at 2-8° C. that is measurable by HPSEC.

This result regarding the RSA characteristics of this antibody in a non-sucrose formulation was further confirmed by analytical ultracentrifugation (AUC) at both temperatures. As shown in FIG. 1B, MabA in this formulation and at 5° C. sediments over a much wider range of sedimentation coefficient distribution than MabA at 25° C., suggesting a significantly different size distribution of the molecules under the two different conditions. In particular, this result indicates a greater RSA tendency of the antibody molecules in this non-sucrose containing formulation at 5° C.

MabA RSA Tendency is Eliminated in the Sucrose-Containing Formulation

Either 20 mg/ml or 50 mg/ml of MabA was reformulated in 50 mM Na-acetate, 10% (w/v) sucrose, 0.05% (w/v) PS80 at pH 5.5, and evaluated by HPSEC at 2-8° C. FIG. 2A indicates a clear absence of a leading edge shoulder on the monomer peak which was prominent in the formulation lacking sucrose at 2-8° C. (compared to FIG. 1A). This is consistent with reduced RSA tendency of MabA in the sucrose-containing formulation, despite the fact that the antibody was present at a higher concentration in the sucrose-containing formulation. Moreover, the reduction in RSA is also observed at a significantly higher concentration of the antibody (50 mg/ml versus 10 mg/ml in FIG. 1A). Accordingly, RSA of MabA in the sucrose-containing formulation does not depend on antibody concentration and is reduced relative to the initial formulation.

Further, the antibody was evaluated by analytical ultracentrifugation at 5° C. and 25° C. In contrast to what was observed for MabA in the non-sucrose containing acetate/salt formulation, MabA in the sucrose-containing formulation behaved similarly at both 5° C. and 25° C.—a result which is also consistent with the elimination of RSA tendency in the sucrose-containing formulation. As shown in FIG. 2B, MabA has similar sedimentation coefficient distributions at both temperatures, indicating that the RSA tendency of MabA in the sucrose-containing formulation does not depend on temperature.

Example 3

RSA of MabA is Driven by Hydrophobic Interactions and is Correlated to its Hydrodynamic Radius RSA is enhanced, in part, "by the exposure of hydrophobic surfaces and the ensuing hydrophobic intermolecular interactions. An evaluation of the interaction between a fluorescent dye (1-anilino-8-naphthalene sulfonate; "ANS") with MabA illustrates this. ANS binds preferentially to hydrophobic patches on a protein surface, which results in an increase in ANS fluorescence intensity. Thus, a decrease in ANS fluorescence intensity is indicative of a decrease in available hydrophobic surfaces and correlates to a decrease in hydrodynamic radius.

As demonstrated in FIG. 3, the interactions between ANS and hydrophobic surfaces on MabA diminish when assessed in formulations having increased sucrose content. This is consistent with the conclusion that the antibody becomes progressively more compact when present in formulations having increased sucrose concentration, as assessed at 5° C. (e.g., assessed at a temperature where RSA tendency, if present, is a significant issue).

In further support of this observation, the overall size of the antibody was evaluated in acetate/salt or sucrose-containing formulations. In particular, the hydrodynamic radius of a protein can be measured as an indicator of the gross conformational changes in the molecule that coincides with changes in surface hydrophobicity. To examine the effect of formulation and temperature on the hydrodynamic radius of MabA, the antibody was evaluated by dynamic light scattering (DLS) at various temperatures in acetate/salt or sucrose-containing formulations.

The hydrodynamic radius of MabA in acetate/salt formulation, pH 7.2, as determined by DLS, decreased with increasing temperature (FIG. 4A). This is consistent with the expected behavior of high RSA tendency (e.g., significant RSA at lower temperatures which decreases after incubation at higher temperatures). In contrast, the hydrodynamic radius was not influenced by temperature (5° C. or 25° C.) in the sucrose-containing formulation (FIG. 4B), suggesting the elimination of the RSA tendency of MabA in this formulation, as RSA tendency is not detected and is comparable at both 5° C. and at 25° C. Note that elimination of RSA tendency of an antibody in a formulation may be evaluated by assessing whether RSA is measurable by HPSEC at 2-8° C. at a given concentration, such as 10 mg/ml.

Example 4

Stabilizing Effects of the Sucrose-Containing Formulation on MabA

As detailed above, MabA, provided in the sucrose-containing formulation of 50 mM sodium-acetate, 10% (w/v) sucrose, 0.05% (w/v) polysorbate 80, pH5.5, has better RSA properties, such as the elimination of RSA tendency relative to the antibody in non-sucrose containing formulations. The following experiment was performed to evaluate thermal stability of the antibody in the improved sucrose-containing formulation.

The thermal transitions of MabA were evaluated by differential scanning calorimetry in the sucrose-containing formulation and compared to that in a non-sucrose-containing formulation of 50 mM sodium-acetate, 100 mM NaCl, 0.01% (w/v) polysorbate 80, pH 5.5, to monitor the conformational stability as a function of temperature. Sample analysis was conducted with the Origin VP-DSC Software to determine the thermal transitions (Tm) on the Fc and Fab regions of the molecule. As shown in FIG. 5, MabA, provided in the sucrose-containing formulation, exhibited a significantly higher Tm, suggesting that the sucrose-containing formulation confers stabilizing effects on the antibody.

To determine the effect of sucrose on the protein-protein (or antibody-antibody) and protein-excipient interactions in solution, the second virial coefficient was examined. As shown in FIG. 6, formulation conditions that have been shown to eliminate RSA tendency (e.g., 12% sucrose in acetate buffer at pH 5.5) produced a net-repulsive second virial coefficient, an observation consistent with the reduction of short-range intermolecular interactions, suggesting the elimination of antibody RSA tendency in such formulations. The protein-protein net-repulsive second virial coefficient appeared to increase with increasing sucrose content. In contrast, the absence of sucrose produced a protein-protein interaction with a net-attractive charge, consistent with the increase in short-range intermolecular interaction, suggesting the increased tendency for MabA to self-associate (i.e., greater RSA) in formulations that lack sucrose.

Methods

The foregoing experiments were performed using, for example, methods described briefly below.

High Performance Size Exclusion Chromatography (HPSEC)

HP-SEC samples were analyzed without room temperature equilibration and run under diluted (10 mg/ml) and target drug product (20 mg/ml) concentrations. The dilutions were prepared with cold formulation buffer (2-8° C.) and loaded into the auto-sampler of the HPLC. The samples were incubated in the auto-sampler (maintained at 5° C.) for approximately 1 hour prior to analysis. Cooled samples were injected onto a TSKgel G3000SWXL column (7.8 mm×30 cm). Samples eluted isocratically with 0.1 M disodium phosphate containing 0.1 M sodium sulfate and 0.05% sodium azide, pH 6.8, at a flow rate of 1.0 ml/minute. The eluted protein was detected using UV absorbance at 280 nm. The results are reported as the area percent of the product monomer peak compared to all other peaks, excluding the buffer-related peak observed at approximately 12 minutes. Peaks eluting earlier than the monomer peak are recorded as percent aggregate. Peaks eluting after the monomer peak are recorded as percent fragment/other.

Dynamic Light Scattering (DLS)

The protein size distribution and molecular size were monitored by dynamic light scattering (DLS) using a Zetasizer Nano ZS (Malvern Instruments, Malvern, Pa.). This instrument incorporates noninvasive backscattering optics that can measure protein sizes in the range of 0.6 nm to 6 μm. DLS measures the time-dependent fluctuations in the intensity of scattered light due to Brownian motion of the protein molecules. The analysis of these intensity fluctuations enables the determination of the diffusion coefficients of particles, which are mathematically converted to an average apparent hydrodynamic diameter of an equivalent sphere using the Strokes Einstein relationship. The diffusion coefficient is calculated from the time correlation function. To understand the reversible self-association of proteins, the time-dependent auto-correlation function of the photocurrent was acquired every 10 seconds, with greater than 10 acquisitions for each run. The sample solution was illuminated using a 633 nm laser, and the intensity of scattered light was measured at an angle of 173 degrees. Samples analyzed at room temperature were incubated on the laboratory bench top for approximately 90 minutes prior to sampling. Cold temperature controlled samples were removed from refrigerated conditions, placed on cold metal block and transferred to the sampling cuvette. The instrument was set to a temperature range of 5° C. and condensation was controlled with nitrogen purge. Prior to each sample analysis, correction factors are input for parameters such as viscosity, refractive index and absorbance. DLS measurements can provide accurate estimates of both hydrodynamic diameter and its Gaussian distribution, which can be used to monitor potential self-association behavior.

Analytical Ultra-Centrifugation (AUC)

AUC experiments were performed by the Analytical Biochemistry Department using a Beckman Optima XL-I analytical ultracentrifuge. The sedimentation velocity experiment samples are diluted to 0.5 mg/ml with appropriate formulation buffer and the resulting protein solutions are loaded in a 12 mm centrifuge cells in the sample channel. Additionally, reference buffer is loaded into the reference channel of each cell. Loaded cells are placed into an AN-50Ti analytical rotor and equilibrated to 25° C. The samples are scanned under a rotor speed of 42,000 rpm while the optical density at 280 nm is measured. The samples are centrifuged at 42,000 rpm until 200 scans are completed. Three repetitions are performed. The data are analyzed using the c(s) method, which is used in standard AUC analysis, with a SEDFIT (version 11.3) program (Dam and Schuck, 2004). In this approach, raw data scans are directly fitted to derive a distribution of sedimentation coefficients.

For the characterization of self-associated monomer, AUC experiments are performed at various protein concentrations and at temperatures of 25° C. and 4° C. Concentrations above 2.0 mg/ml are examined with Rayleigh interference optics in 3 mm path length centrifuge cells. Samples are dialyzed for a minimum of 12 hours, and the dialysate is used for dilutions and for loading of the reference sector. When experiments were performed at 4° C., all dialysis, sample dilution, cell loading, and rotor loading were performed in a cold room (2-8° C.) and the centrifuge was pre-cooled so that the sample remained at 2-8° C. during the entire experiment. The samples are centrifuged at 42,000 RPM while the refractive increment versus radial position is collected by the Rayleigh interferometry system. Scans are collected continuously until the sample is sedimented to the bottom of the cell. The number of scans collected is 500 to 999, depending on the conditions. AUC data of the self-associated monomer are analyzed using the g(s) method and not the c(s) method described above. The g(s) method is appropriate for analysis of interacting self-associating species, which cannot be achieved by the c(s) method. However, this method results in relatively broad overlapping peaks. The AUC raw data are transformed into apparent sedimentation coefficient distributions [g(s) plots] by the SEDANAL program (Stafford and Sherwood).

Fluorescence Measurements

The interaction of the fluorescent dye ANS with proteins was analyzed with the Photon Technology International (PTI) Quanta Master fluorometer. ANS (1-anilino-8-naphthalene sulfonate) fluorescent dye is known to preferentially bind to hydrophobic patches on protein surfaces. Binding results in an increase in ANS fluorescence intensity. A comparison of ANS fluorescence intensity under similar conditions can be used to detect very small conformational changes in a protein which might be beyond the detection limits of other methods.

The PTI is equipped with a Turret 400, thermostatically controlled holder connected to a circulating water bath, and fluorescence measurements were conducted in quartz optical cells of 10 mm path length. Excitation wavelength was set at 400 nm and emission was recorded in the range of 400-600 nm. Every 0.5 nm was recorded at a rate of 1nm per second. Emission/Excitation slits widths were set at 4 and 3 nm respectively.

Protein and ANS (Invitrogen) stock solution in HPLC water were mixed in micro-centrifuge tubes and incubated overnight in the dark at both room and refrigerated temperatures. The protein concentration used for this experiment was 0.5 mg/ml, and the amount of ANS required was based on the in-excess molar ration of 100 moles of ANS to 1 mole of protein. For cold temperature (5° C.) analysis, the prepared samples were placed on cold metal block and then transferred into the quartz cuvette and placed into the temperature-controlled sample compartment of the PTI spectrometer. The fluorescence spectra were recorded after approximately 5 minutes of additional incubation at 5° C. in the sample compartment. For room temperature (25° C.) analysis, the samples are transferred to the quartz cuvettes and incubated under ambient conditions in the sample compartment (at 25° C.) for 5 minutes prior to testing. The fluorescence measurements with ANS can provide an assessment of the surface hydrophobicity.

Differential Scanning Calorimetry

Differential scanning calorimetry (DSC) was applied to monitor the conformational stability as a function of temperature. DSC experiments were performed with the VP-Capillary DSC manufactured by Micro calorimetry. Run parameters include a scanning range of 20° C. to 120° C. at a rate of 60 deg/hr. Samples were prepared to approximately 0.5 mg/ml in corresponding buffers and sample wells were filled to a 400 µl fill volume. Additional samples of buffer and water were included in the run as a baseline and wash steps respectively. Sample analysis was conducted with the Origin VP-DSC Software to determine the thermal transitions (Tm) on the Fc and Fab regions of the molecule. At higher thermal transitions, the more protein remains in a native (folded state), which translates into increased thermal stability.

Incorporation by Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

Citation or discussion of a reference herein shall not be construed as an admission that such is prior art to the present invention.

We claim:

1. A formulation, comprising:
   a) an aqueous carrier;
   b) 1 mg/ml to 100 mg/ml of an antibody or antibody fragment that specifically binds to PDGFR-alpha and inhibits growth of cells that express PDGFR-alpha, wherein said antibody or antibody fragment in said formulation has substantially similar reversible self-association (RSA) characteristics at 2-8° C. and 23-27° C., as determined by analytical ultracentrifugation (AUC);
   c) 4% to 20% (weight/volume) sucrose;
   d) 0.01% to 0.1% (weight/volume) polysorbate 80 (PS80); and
   e) sodium-acetate buffer,
   wherein said formulation has a pH of pH 4.0 to pH 6.0.

2. The formulation of claim 1, wherein said antibody or antibody fragment is present at a concentration of from 20 mg/ml to 50 mg/ml.

3. The formulation of claim 1, wherein the antibody or antibody fragment comprises
   a VH CDR1 having the amino acid sequence of SEQ ID NO: 3;
   a VH CDR2 having the amino acid sequence of SEQ ID NO: 4;
   a VH CDR3 having the amino acid sequence of SEQ ID NO: 5:
   a VL CDR1 having the amino acid sequence of SEQ ID NO: 6;
   a VL CDR2 having the amino acid sequence of SEQ ID NO: 7; and
   a VL CDR3 having the amino acid sequence of SEQ ID NO: 8.

4. The formulation of claim 1, comprising 10% (w/v) sucrose.

5. The formulation of claim 1, wherein the formulation is substantially free of histidine.

6. The formulation of claim 1, wherein the formulation is substantially free of any additional surfactant.

7. The formulation of claim 1, wherein the formulation is substantially free of any additional saccharide or polyol.

8. A formulation, consisting essentially of:
   a) sterile water;
   b) 20 mg/ml of an antibody or antibody fragment that specifically binds to PDGFR-alpha and inhibits growth of cells that express PDGFR-alpha;
   c) 10% (weight/volume) sucrose;
   d) 0.05% (weight/volume) polysorbate 80 (PS80); and
   e) 50 mM sodium-acetate buffer,
   wherein said formulation has a pH of pH 5.5.

9. The formulation of claim 8, wherein the antibody or antibody fragment comprises
   a VH CDR1 having the amino acid sequence of SEQ ID NO: 3;
   a VH CDR2 having the amino acid sequence of SEQ ID NO: 4;
   a VH CDR3 having the amino acid sequence of SEQ ID NO: 5:
   a VL CDR1 having the amino acid sequence of SEQ ID NO: 6;
   a VL CDR2 having the amino acid sequence of SEQ ID NO: 7; and
   a VL CDR3 having the amino acid sequence of SEQ ID NO: 8.

10. The formulation of claim 8, wherein the formulation is not suitable for lyophilization.

11. A formulation, comprising:
    a) an aqueous carrier;
    b) 1 mg/ml to 100 mg/ml of an antibody or antibody fragment;
    c) 4% to 20% (weight/volume) sucrose;
    d) 0.01% to 0.1% (weight/volume) polysorbate 80 (PS80); and
    e) sodium-acetate buffer, wherein said formulation has a pH of pH 4.0 to pH 6.0, and wherein said antibody or antibody fragment in said formulation has substantially the same non-RSA tendency when evaluated at about 2-8° C. versus at about 23-27° C.

12. A formulation, comprising:
   a) an aqueous carrier;
   b) 1 mg/ml to 100 mg/ml of an antibody or antibody fragment;
   c) 4% to 20% (weight/volume) sucrose;
   d) 0.01% to 0.1% (weight/volume) polysorbate 80 (PS80); and
   e) sodium-acetate buffer,
wherein said formulation has a pH of pH 4.0 to pH 6.0, and wherein greater than 95% of said antibody or antibody fragment in said formulation is in non-self-associated, monomeric form at 2-8° C.

13. A formulation comprising an antibody or antibody fragment produced according to a method for eliminating or reducing reversible self-association (RSA) of an antibody in a formulation, said method comprising
   providing an initial formulation comprising the antibody or antibody fragment, wherein RSA of said antibody or antibody fragment in said initial formulation is measurable by HPSEC (i) at approximately 2-8° C. and/or (ii) at a concentration of greater than 4 mg/ml, and which antibody or antibody fragment in said initial formulation contains high molecular weight forms;
   adding sucrose to said initial formulation to provide an altered formulation having about 4% to about 20% (weight/volume) sucrose,
wherein RSA of the antibody or antibody fragment in the altered formulation is eliminated or reduced relative to that of the initial formulation, when compared at a given antibody concentration at approximately 2-8° C.

14. The formulation of claim 1, comprising 6% to 12% (w/v) sucrose.

* * * * *